US006573418B2

(12) United States Patent
Miller et al.

(10) Patent No.: US 6,573,418 B2
(45) Date of Patent: Jun. 3, 2003

(54) PROCESS FOR PRODUCTION OF PARA-XYLENE INCORPORATING PRESSURE SWING ADSORPTION AND SIMULATED MOVING BED ADSORPTION

(75) Inventors: Jeffrey T. Miller, Naperville, IL (US); Bryce A. Williams, Lisle, IL (US); Ruth Ann Doyle, Oswego, IL (US); Giorgio Zoia, Chicago, IL (US)

(73) Assignee: BP Corporation North America Inc., Chicago, IL (US)

( * ) Notice: Subject to any disclaimer, the term of this patent is extended or adjusted under 35 U.S.C. 154(b) by 23 days.

(21) Appl. No.: 09/901,813

(22) Filed: Jul. 10, 2001

(65) Prior Publication Data

US 2002/0077519 A1 Jun. 20, 2002

Related U.S. Application Data

(60) Provisional application No. 60/238,217, filed on Oct. 5, 2000, and provisional application No. 60/220,536, filed on Jul. 10, 2000.

(51) Int. Cl.[7] .............................. C97C 7/12; C97C 5/22
(52) U.S. Cl. ....................... 585/826; 585/820; 585/825; 585/827; 585/828; 585/805; 585/477; 585/478
(58) Field of Search ................................. 585/820, 822, 585/825, 826, 827, 828, 805, 477, 478

(56) References Cited

U.S. PATENT DOCUMENTS

| 2,985,589 A | 5/1961 | Broughton et al. ............ 210/34 |
| 3,201,491 A | 8/1965 | Stine et al. .................. 260/676 |
| 3,626,020 A | 12/1971 | Neuzil ......................... 260/674 |
| 3,653,184 A | 4/1972 | Drinkard et al. ............... 55/67 |
| 3,656,278 A | 4/1972 | Drinkard et al. ............... 55/67 |

(List continued on next page.)

FOREIGN PATENT DOCUMENTS

| CN | 1136549 | 11/1996 |
| EP | 138617 | 4/1985 |
| EP | 923512 | 6/1999 |
| FR | 2757507 | 12/1996 |
| GB | 1420796 | 1/1976 |

OTHER PUBLICATIONS

Namba, S., et al., "Novel purification method of commercial o–and m–xylenes by shape selective adsorption on HZSM–5", Microporous Materials, 8, 39 (1997).

Yan, T. Y., "Separation of p–Xylene and Ethylbenzene from C8 Aromatics Using Medium–Pore Zeolites", Ind. Eng. Chem. Res., 28,: 572–576 (1989).

Choudhary, V. R., et al., "Single–Component Sorption/Diffusion of Cyclic Compounds from Their Bulk Liquid Phase in H–ZSM–5 Zeolite", Ind. Eng. Chem. Res., 36,: 1812–1818 (1997).

Wu, E. L., et al., "Hydrocarbon Adsorption Characterization of Some High Silica Zeolite", Stud Surf. Sci. Catal. 28, 547 (1996).

*Primary Examiner*—Walter D. Griffin
*Assistant Examiner*—Tam M. Nguyen
(74) *Attorney, Agent, or Firm*—Mary Jo Kanady; Thomas A. Yassen

(57) ABSTRACT

A pressure swing adsorption process to separate para-xylene and ethylbenzene from $C_8$ aromatics which uses a para-selective, non-acidic, medium pore molecular sieve of the MFI structure type and is operated isothermally in the vapor phase at elevated temperatures and pressures is integrated with simulated moving bed adsorption (SiMBAC) to produce para-xylene product. A fixed bed of adsorbent is saturated with pX and EB, which are preferentially adsorbed, the feed is stopped, and lowering the partial pressure desorbs the pX and EB. The process effluent, which is rich in pX and EB, is subjected to SiMBAC to obtain para-xylene product.

45 Claims, 12 Drawing Sheets

U.S. PATENT DOCUMENTS

| | | | |
|---|---|---|---|
| 3,696,107 A | 10/1972 | Neuzil | 260/674 |
| 3,699,182 A | 10/1972 | Cattanach | 260/674 |
| 3,724,170 A | 4/1973 | Allen et al. | 55/67 |
| 3,729,523 A | 4/1973 | Grandio, Jr. et al. | 260/674 |
| 3,770,841 A | 11/1973 | Meyers | 260/668 |
| 3,960,520 A | 6/1976 | Allen | 55/59 |
| 4,039,599 A | 8/1977 | Gewartowski | 260/668 |
| 4,098,836 A | 7/1978 | Dywer | 260/668 |
| 4,184,943 A | 1/1980 | Anderson | 208/310 |
| 4,381,419 A | 4/1983 | Wylie | 585/828 |
| 4,402,832 A | 9/1983 | Gerhold | 210/659 |
| 4,453,029 A | 6/1984 | Dessau | 585/828 |
| RE31,782 E | 12/1984 | Olson et al. | 585/481 |
| 4,899,017 A | 2/1990 | Yan | 585/828 |
| 4,899,901 A | 2/1990 | Chu et al. | 585/481 |
| 4,908,342 A | 3/1990 | McWilliams et al. | 502/58 |
| 5,001,296 A | 3/1991 | Howley et al. | 585/489 |
| 5,028,573 A | 7/1991 | Brown et al. | 502/66 |
| 5,284,992 A | 2/1994 | Hotier et al. | 585/805 |
| 5,329,060 A | 7/1994 | Swift | 585/805 |
| 5,367,099 A | 11/1994 | Beck et al. | 585/475 |
| 5,908,967 A | 6/1999 | Benazzi et al. | 585/481 |
| 5,922,924 A | 7/1999 | Hotier et al. | 585/479 |
| 5,948,950 A | 9/1999 | Hotier et al. | 585/828 |
| 6,150,292 A | 11/2000 | Merlen et al. | 502/66 |

Pressure Swing Adsorption Cycle with Pressure Equilization

PROCESS FOR PRODUCTION OF PARA-XYLENE INCORPORATING PRESSURE SWING ADSORPTION AND SIMULATED MOVING BED ADSORPTION

This application claims the benefit of U. S. Provisional Application No. 60/220,536 filed Jul. 10, 2000, and U.S. Provisional Application No. 60/238,217 filed Oct. 5, 2000, which are incorporated herein by reference in their entireties.

BACKGROUND OF THE INVENTION

The present invention relates to a process for producing para-xylene incorporating pressure swing adsorption and simulated moving bed (liquid chromatography) purification. The present invention includes a pressure swing adsorption (PSA) process component for separating para-xylene and ethylbenzene from mixed $C_8$ aromatics using a para-selective adsorbent. The para-selective adsorbent is preferably a non-acidic, molecular sieve. The para-selective adsorbent is more preferably a non-acidic, medium pore, molecular sieve. The molecular sieve is preferably of the MFI structure type and the process is preferably operated in the vapor phase at elevated temperatures and pressures wherein the temperature is substantially isothermal. The present invention also relates to a method of pressure swing adsorption which includes a plurality of steps and which provides recovery from a mixture comprising $C_8$ aromatics of a substantially pure para-xylene or para-xylene and ethylbenzene product stream and a substantially pure meta-xylene and ortho-xylene product stream.

It is known that certain high surface area, porous substances such as silica gel, activated charcoal, and molecular sieves, including zeolites and other molecular sieves, have certain selective adsorption characteristics useful in separating a hydrocarbon mixture into its component parts.

The selective sorption properties of molecular sieves and zeolites have been disclosed in earlier patents and in literature references. Crystalline molecular sieves and zeolites are shape-selective in that they will admit molecules of specific geometry while excluding other molecules.

The separation of xylene isomers has been of particular interest because of the usefulness of para-xylene in the manufacture of terephthalic acid which is used in the manufacture of polyester fabric. Other components of the $C_8$ aromatic hydrocarbon feedstream from which para-xylene (pX) is generally produced are ortho-xylene (oX), which is used in the manufacture of phthalic anhydride which is used to make phthalate based plasticizers; meta-xylene (mX), which is used in the manufacture of isophthalic acid used in the production of specialty polyester fibers, paints, and resins; and ethylbenzene (EB) which is used in the manufacture of styrene.

A refinery feedstock of aromatic $C_8$ mixtures containing ethylbenzene and xylenes will typically have the following content:

| | |
|---|---|
| ethylbenzene | about 0 wt % to about 50 wt % |
| para-xylene | about 0 wt % to about 25 wt % |
| ortho-xylene | about 0 wt % to about 35 wt % |
| meta-xylene | about 20 wt % to about 90 wt % |
| non-aromatics | about 0 wt % to about 10 wt % |
| $C_9^+$ aromatics | about 0 wt % to about 30 wt % |

Equilibrium mixtures of $C_8$ aromatic hydrocarbons generally contain about 22 weight percent para-xylene, about 21 weight percent ortho-xylene, and about 48 weight percent meta-xylene in the equilibrium mixture.

Processes to separate xylene isomers include low temperature crystallization, fractional distillation, selective sulfonation with subsequent hydrolysis and selective solvent separation; however, such processes require high operating costs.

The use of faujasite zeolites, which are large pore type X and Y type zeolites, as adsorbents in liquid phase, chromatographic-type separations is well known.

In the petrochemical production chain, one of the most important streams is the $C_6$ to $C_8$ aromatics stream containing benzene, toluene, and xylenes (BTX), which is a source of raw materials for high value downstream products. Of the $C_8$ aromatics, para-xylene (pX) is the most desirable. However, because the boiling points of ethylbenzene (EB), ortho-xylene (oX), meta-xylene (mX) and para-xylene (collectively referred to as "$C_8$ aromatics") are close, they are difficult to separate by fractional distillation. As a consequence, various alternative methods of separating pX from the $C_8$ aromatics have been developed. Common separation methods are fractional crystallization, which utilizes the difference in freezing points, and liquid phase adsorption (e.g., UOP's Parex process and IFP's Eluxyl process), which uses a faujasite zeolite to chromatographically separate pX from the other $C_8$ aromatics. The reject stream from the crystallization process or the raffinate from the adsorption process are depleted in pX, and contain relatively high proportions of EB, oX and mX. These streams are typically sent to a catalyst reactor, where the xylenes are isomerized to equilibrium, and at least a portion of the EB is converted to other products, which can be removed from the $C_8$ aromatics by fractional distillation.

Processes for making pX have typically included combinations of isomerization with fractional crystallization or adsorption separation. FIG. 1 is a schematic representation of known art combination of an isomerization catalyst reactor and a crystallization unit. Crystallization is a separation process that takes advantage of the fact that pX crystallizes before the other isomers, i.e., pX crystallizes at 13.3° C. (55.9° F.), whereas oX crystallizes at −25.2° C. (13.4° F.) and mX at −47.9° C. (−54.2° F.). In the physical system of the three isomers, there are two binary eutectics of importance, the pX/mX and the pX/oX. As pX is crystallized from the mixture, the remaining mixture (mother liquor) composition approaches one of these eutectic binaries, depending on the starting composition of the mixture. Therefore, in commercial practice, pX is crystallized so that the binary eutectic is only approached but not reached to avoid co-crystallization of the xylene isomers, which would lower the pX purity. Thus, the key disadvantage for crystallization is restricted pX recovery per pass, due to this eutectic limit of the $C_8$ stream. Typically, the concentration of pX in a mixed $C_8$ aromatic stream at equilibrium is about 22 wt %. In commercial crystallization operations, the eutectic point of this mixture limits the pX removed per pass to about 65% of that amount.

The problem of the eutectic limit for pX crystallization has been recognized for some time. U.S. Pat. No. 5,329,060 discloses that the eutectic point of the crystallization unit can be overcome by use of a selective adsorption zone that enriches the pX feed to the crystallizer by rejecting most of the mX, oX and EB to the isomerization reactor. Specifically, the disclosure teaches using a faujasite-based, liquid phase adsorption process that can either be selective for pX or selective for mX and oX. The result of this process is a stream enriched in pX, but still containing a substantial portion of mX and oX. Similarly, U.S. Pat. No. 5,922,924 discloses combining at least one liquid phase, simulated moving bed adsorption zone with crystallization to produce high purity pX. Again, pX is enriched, but the stream still contains significant mX and oX.

U.S. Pat. No. 3,699,182 discloses use of zeolite ZSM-5 in a process for selective separation of biphenyls from mixtures containing the same and para-disubstituted aromatic isomers from mixtures containing the same, particularly for separating $C_8$ aromatics using ZSM-5 zeolite.

U.S. Pat. No. 3,724,170 discloses chromatographic separation of C8 aromatic mixtures over zeolite ZSM-5 or ZSM-8, which has preferably been reacted with an organic radical-substituted silane, in at least two distinct stages whereby para-xylene and ethylbenzene are selectively absorbed whereas the meta-xylene and ortho-xylene are not adsorbed, removing the unadsorbed meta-xylene and ortho-xylene, eluting the para-xylene followed by the ethylbenzene.

British Pat. No. 1,420,796 discloses use of zeolite ZSM-5 or ZSM-8, preferably ZSM-5 or ZSM-8 zeolites which have been reacted with certain silanes, for adsorptive separation of para-xylene and ethylbenzene from a mixture of para-xylene, ortho-xylene, meta-xylene, and ethylbenzene by adsorption/desorption using two or more columns operated in a parallel manner so that when adsorption is being conducted in one column, desorption can be conducted in a parallel column under such conditions as to obtain a continuously operating process which is said to have faster results than use of a single column alone. It is stated that 250° C. (482° F.) is a preferred upper limit as operation above 250° C. (482° F.) may lead to catalytic conversion in the zeolite-containing column.

U.S. Pat. No. 3,729,523 discloses a process for separating and recovering each of the xylene isomers and ethylbenzene wherein a mixture of $C_8$ aromatic hydrocarbons, which may also contain $C_9$ and higher paraffins, is heated to 50° F.–500° F. (10° C.–260° C.) and subjected to an adsorption step to recover a first mixture of para-xylene and ethylbenzene and a second mixture comprising meta-xylene, ortho-xylene, and the $C_9$ and higher aromatics. The adsorption is preferably conducted in the presence of a molecular sieve or synthetic crystalline aluminosilicate zeolite as the adsorbent, with ZSM-5, the preferred zeolite. The para-xylene and ethylbenzene are adsorbed and may be recovered by heating the adsorbent, reducing the partial pressure of the sorbed material in the vapor or liquid surrounding the adsorbent, lowering the total pressure of the system or purging with a suitable inert gas or displacement liquid. The resulting para-xylene and ethylbenzene mixture is then subjected to crystallization to recover para-xylene and the mother liquor is subjected to distillation to recover the ethylbenzene.

Chinese Patent Application No. 1136549 discloses selectively adsorbing pX and EB from a $C_8$ isomer stream using silicalite-1 zeolite and then producing >99.5% purity mX and oX from the portion of the stream not adsorbed. In this process there is a substantial amount of contaminating feedstream in the voids of the silicalite-1 adsorbent which is not removed and comes off the adsorption bed along with the adsorbed pX and EB so that the desorbed stream is not substantially pure pX and EB but contains significant amounts of unseparated oX and mX.

None of these references discloses a process using pressure swing adsorption employing a para-selective adsorbent which is preferably a large crystal, non-acidic medium pore molecular sieve in connection with simulated moving bed adsorption chromatography to effectively separate and produce pure para-xylene in high yield.

Molecular sieves are crystalline oxides having pore openings and internal cavities the size of some molecules. Zeolites, a sub-group of molecular sieves, are crystalline aluminosilicates. Another well-known sub-group of molecular sieves are aluminophosphates or ALPOs. In general, molecular sieves are classified into three groups based on pore size: small pore molecular sieves with pore diameters from 3–4 Å; medium pore molecular sieves with pores diameters from 4–6 Å; and large pore molecular sieves with pore openings of 6–8 Å. In addition to the molecular size pores, molecular sieves have high adsorption energies and for many years have been used as adsorbents. By selection of the proper pore size, molecular sieves may selectively adsorb molecules of different size. This molecular sieving leads to adsorption and separation of the smaller molecule. Often molecular sieving selectivities are high, 100 or greater. The separation of branched from linear paraffins is a commercial process, which utilizes the small pore A zeolite.

Large pore molecular sieves have also been utilized in the separation of hydrocarbons. In large pore molecular sieves, however, all components diffuse into the pores and the separation is based on differences in adsorption energies. The molecule with the highest bond energy is preferentially adsorbed. Generally, adsorption selectivities are high only when molecules have very different heats of adsorption, for example water and paraffin. For molecules with similar heats of adsorption, the adsorption selectivities are low, ca. 1–4. Xylenes isomers, for example, have similar heats of adsorption in Y zeolite. Due to small differences in heats of adsorption and packing geometry in BaY, pX displays an adsorption selectivity of about 2 compared with the other $C_8$ aromatics. In order to separate pX in sufficient purity for chemical sale, i.e., greater than 99%, many separation stages must be conducted. This type of process operates on principles similar to that of chromatography. Commercial examples of separations of this type are the UOP Parex and IFP Eluxyl liquid phase adsorption processes, which utilize ion exchanged Y zeolites to separate pX from $C_8$ aromatics.

Adsorbents useful in the present invention are based on molecular sieves that selectively adsorb p-xylene within the channels and pores of the molecular sieve while not effectively adsorbing m-xylene and o-xylene $C_8$ isomers (i.e., total exclusion of the larger m-xylene and o-xylene or having much slower adsorption rates compared to p-xylene.).

Molecular sieves are ordered porous crystalline materials, typically formed from silica, alumina, and phosphorus oxide ($PO_4$) tetrahedra, that contain a crystalline structure with cavities interconnected by channels. The cavities and channels within the crystalline structure are uniform in size and may permit selective separation of hydrocarbons based upon molecular dimensions. Generally, the term "molecular sieve" includes a wide variety of natural and synthetic crystalline porous materials which typically are based on silica tetrahedra in combination with other tetrahedral oxide materials such as aluminum, boron, titanium, iron, gallium, and the like. In these structures networks of silicon and elements such as aluminum are cross-linked through sharing of oxygen atoms. Substitution of elements such as aluminum or boron for silicon in the molecular sieve structure produces a negative framework charge which must be balanced with positive ions such as alkali metal, alkaline earth metal, ammonium or hydrogen. Molecular sieve structures also may be formed based on phosphates in combination with other tetrahedrally substituted elements such as aluminum.

Adsorbents useful in this invention should not possess catalytic isomerization or conversion activity with respect to the $C_8$ aromatic feedstream. Thus, suitable molecular sieves should be non-acidic. If an element such as aluminum or gallium is substituted in the molecular sieve framework, the sieve should be exchanged with a non-acidic counter-ion, such as sodium, to create a non-acidic sieve adsorbent.

Examples of molecular sieves suitable as adsorbents useful in this invention include zeolitic materials containing pore dimensions in the range of 5 to 6 Å ($10^{-8}$ meter), typically 5.1 to 5.7 Å, and preferably 5.3 to 5.6 Å, as measured in cross axes of the pore. This range typically is referred to as "medium pore" and typically contains 10-ring tetrahedra structures. Typical examples of medium pore molecular sieves include those with MFI and MEL framework structures as classified in Meier and Olson, "Atlas of Zeolite Structure Types," International Zeolite Association (1987), incorporated herein by reference in its entirety. A small pore molecular sieve, such as A zeolite, which contains 8-ring structures does not have a sufficiently large pore opening to effectively adsorb para-xylene within the sieve. Most large pore molecular sieves, such as mordenite, Beta, LTL, or Y zeolite, that contain 12-ring structures do not adsorb para-xylene selectively with respect to ortho- and meta-xylenes. However, several 12 ring structures, having a smaller effective pore size, for example due to puckering, are potentially useful in the invention, such as structure types MTW (e.g., ZSM-12) and ATO (e.g., ALPO-31).

Specific examples of molecular sieves include ZSM-5 (MFI structure type) and ZSM-11 (MEL structure type) and related isotypic structures. Since suitable adsorbents should not be catalytically reactive to components in the feedstream, the preferable adsorbent useful in this invention is silicalite (MFI structure type), an essentially all silica molecular sieve, which contains minimal amounts of aluminum or other substituted elements. Typically, the silica/alumina ratio of suitable silicalite is above 200 and may range above 1000 depending on the contaminant level of aluminum used in the sieve's preparation. Other MFI and MEL sieves may be use to the extent they are made non-catalytically active. MFI-based molecular sieves are preferred in this invention with silicalite as the most preferred. Other potentially useful adsorbents include structure types MTT, FER, EUO, MFS, TON, AEL, ATO, NES, and others with similar pore sizes.

A molecular sieve which is not catalytically reactive will typically exhibit less than 10% conversion of pX to mX and oX, and preferably less than 5%, and most preferably less than 1%, at the temperature of operation for the process of the invention.

Attempts have been made to use adsorption with zeolites such as ZSM-5 and ZSM-8 to separate ethylbenzene (EB), para-xylene (pX), meta-xylene (mX), and ortho-xylene (oX) from mixtures of $C_8$ aromatics; however, a major disadvantage of these processes is that the time required to effect desorption of the adsorbed components is too long to provide a commercially useful process. In addition, with acidic zeolites, such as HZSM-5, the high temperatures used to obtain rapid desorption cause catalytic reactions to occur converting pX to mX and oX and converting EB to benzene. Furthermore, with HZSM-5, traces of olefins, which are usually present in commercial feeds, irreversibly chemisorb lowering the adsorption capacity of the zeolite. As a result, frequent reconditioning of the adsorbent (e.g., removal of coke deposits) is required.

Due to the strong adsorption and reactivity of xylenes on acid sites of adsorbents such as HZSM-5, a commercial separation process has not been developed. We describe the use of silicalite in a high temperature process to effect the separation of para-xylene and ethylbenzene from a $C_8$ aromatic mixture without reaction of the adsorbed hydrocarbons. These adsorbent and process modifications solve the previous technical obstacles, which have limited commercial development of a molecular sieving, selective adsorption/desorption process for separation of $C_8$ aromatic hydrocarbons.

The process of the present invention overcomes disadvantages of known processes by using pressure swing adsorption at elevated temperature and pressure with a non-acidic, molecular sieve-containing adsorbent to accomplish a rapid adsorption and desorption of the desired components from a feedstream containing $C_8$ aromatics and provide a rapid separation of the desired components which is suitable for commercial use. A non-acidic molecular sieve, such as silicalite (MFI structure type with little to no aluminum), is used to selectively adsorb pX and EB. Desorption is significantly faster and reactions of the adsorbed molecules (pX and EB) do not occur. In addition, olefins do not adsorb on the silicalite, so the adsorption capacity of the adsorbent remains high and frequent reconditioning is not required.

Many of the chemical and physical properties of xylene isomers and ethylbenzene are very similar making separation difficult. The molecular size of these isomers, however, is slightly different and is determined by the position of methyl substitution. The kinetic diameter of para-xylene and ethylbenzene are approximately 6.0 Å; whereas meta-xylene and ortho-xylene are slightly larger, 6.8 Å. It has been known for many years that, based on these differences in size, medium pore zeolites, such as HZSM-5, can selectively adsorb para-xylene and ethylbenzene [See U.S. Pat. Nos. 3,653,184; 3,656,278; 3,770,841; 3,960,520; 4,453,029; 4,899,017; Wu, et al. STUD. SURF. SCI. CATAL., 28:547 (1996); Yan, T. Y., IND. ENG. CHEM. RES. 28:572(1989); and Choudhary, et al., IND. ENG. CHEM. RES. 36:1812 (1997)] However, a disadvantage of using HZSM-5 for such separations is that protonation of the aromatic ring by acid sites in ZSM-5 leads to formation of a strong chemical bond [Farneth, et al., LANGMUIR, 4:152(1988)] resulting in low desorption rates and long desorption times at low temperature. As a result, such excessively large amounts of ZSM-5 would be required for commercial scale separation of para-xylene and ethylbenzene under these conditions that such separations are not commercially feasible. Increasing the desorption temperature does increase the desorption rate, which lowers the amount of adsorbent needed; however, the acid sites on the HZSM-5 zeolite also have catalytic properties which cause undesirable isomerization of para-xylene to meta-xylene and ortho-xylene, significantly reducing para-xylene purity. Another disadvantage is that the acid sites strongly adsorb olefins which are typically present along with the $C_8$ aromatics in the feedstream, thus lowering the capacity of the adsorbent to adsorb para-xylene and ethylbenzene. These olefins can only be desorbed at high temperatures. Thus, there is either a loss of adsorption capacity at low temperature or a loss in selectivity at high temperature due to reactions catalyzed by the acid sites.

Disadvantages of the earlier processes are overcome in the present invention by using a pressure swing adsorption process for separating para-xylene and ethylbenzene from mixed $C_8$ aromatics using a non-acidic, medium pore molecular sieve, preferably of the MFI structure type and preferably operating in the vapor phase at elevated temperatures and pressures.

We have found that non-acidic forms of ZSM-5, such as Na-ZSM-5, are preferred adsorbents over HZSM-5. In particular, silicalite is a preferred adsorbent over HZSM-5. Silicalite, an all silica, isostructural form of ZSM-5 has been shown to possess superior properties. Like ZSM-5, silicalite selectively adsorbs pX and EB; however, desorption is significantly faster, since the molecules are only adsorbed physically not chemically, as with HZSM-5. Moreover, pX does not isomerize, even at the elevated temperatures necessary to make the process economically practicable.

In silicalite, a silica analog of H-ZSM-5, pX and EB are selectively adsorbed due to their smaller size. However, unlike H-ZSM-5, silicalite contains no acid sites. As a result, pX and EB are desorbed at high temperature without reaction. At elevated temperature, the desorption rates are high and the cycle times are much shorter. As a result, much less adsorbent is required. Furthermore, the adsorption capacity does not decrease significantly with repeated adsorption/desorption cycles due to adsorption of olefins in the aromatic stream.

The present invention uses selective adsorption (adsorption of the smaller $C_8$ isomers) and selective desorption (i.e., no isomerization upon desorption) at substantially isothermal temperatures to provide a substantially pure product stream of para-xylene and ethylbenzene and a substantially pure stream of ortho-xylene and meta-xylene. The components in these streams can be further separated to provide substantially pure para-xylene, ethylbenzene, ortho-xylene, and meta-xylene products.

The problems of long desorption times or the need for excessively large amounts of adsorbent have made earlier attempts to separate C8 aromatics by molecular sieving commercially impracticable. In addition to these disadvantages, there is also the problem of how to remove $C_8$ aromatic feed that collects in non-selective voids, that is, feed which collects in the non-selective void volume (i.e., large mesopores in the adsorbent, interstitial space between adsorbent particles, and void space in the adsorbent vessel) so that the purity of the desorbed product stream will not be reduced by this material. The art has not recognized how to overcome this problem for $C_8$ aromatics.

The present invention has solved this problem by selectively separating the $C_8$ aromatic feed that is contained in the non-selective void volume so that a high purity stream of para-xylene and ethylbenzene is obtained following desorption. A high purity stream of mX and oX is also obtained by the process of the invention. In one embodiment of the invention this high purity stream of mX/oX is obtained by separating the mX/oX from the non-selective void volume prior to desorbing the pX/EB.

The use of the PSA process of the present invention in para-xylene production facilities would significantly reduce the amount of meta-xylene and ortho-xylene sent to a simulated moving bed adsorption chromatography (SiMBAC) section, thus opening up capacity and decreasing operating costs. This would increase the para-xylene concentration and yields.

There are two widely practiced processes for the production of para-xylene (pX) from a mixture of $C_8$ aromatics. Each process includes a catalyst section containing one or more catalysts for conversion of a portion of ethyl benzene to benzene, or other products and a catalyst for isomerization of xylenes. Additionally, the process includes distillation towers for removal of components boiling above and below that of the $C_8$ aromatics, and finally, a section for purification and recovery of the para-xylene product, generally at purities greater than 99.5%. The two commercial pX processes differ significantly in the method of purification, i.e., crystallization or selective, liquid-phase chromatographic adsorption (also called simulated moving bed adsorption separation). For the latter purification method, two commercial processes have been developed, one by UOP and one by IFP (U.S. Pat. Nos. 3,729,523, 2,985,589 and 4,402,832 incorporated herein by reference in their entireties. Both purification processes use a Y zeolite ion-exchanged by either K or Ba ions. Continuous liquid chromatography methods have the following characteristics. In order to obtain high purity and high recovery, the adsorbent column must be divided into many beds, which limits the unit productivity. The product recovery is obtained by desorbing the $C_8$ aromatics with a liquid desorbent, generally toluene or p-diethyl benzene, and large amounts of solvent are required to obtain high purity pX. The main disadvantage of this type unit is its high investment cost and complexity of operation. In addition, high energy costs are required to distill the large quantities of (desorbent) solvent from the pX.

This present invention includes a process for production of p-xylene utilizing a pressure swing adsorption process for separation of para-xylene and ethyl benzene from $C_8$ aromatics in combination with a liquid chromatographic (or simulated moving bed) purification process. Several process design embodiments may be included in the invention. Because of the change in the composition of the process streams using the combined PSA separation-liquid chromatographic purification process, improved yields may be obtained when processing the remaining hydrocarbon streams over the xylene isomerization and ethylbenzene dealkylation catalysts of the process. The use of the PSA process of the present invention in para-xylene production facilities would significantly reduce the amount of meta-xylene and ortho-xylene sent to a simulated moving bed liquid chromatographic section, thus opening up capacity and decreasing operating costs. This would increase the para-xylene concentration and yields.

An advantage of the process of the present invention, which integrates PSA with simulated moving bed adsorption, is that existing production facilities using a simulated moving bed adsorption process to separate para-xylene from $C_8$ aromatics may be readily modified to practice the process of the present invention thus improving overall yields and cost efficiency.

SUMMARY OF THE INVENTION

The present invention relates to a process for producing para-xylene incorporating pressure swing adsorption and simulated moving bed (liquid chromatography) purification. The present invention also relates to a pressure swing adsorption (PSA) process component for separating para-xylene, or para-xylene and ethylbenzene, from mixed $C_8$ aromatics using an adsorbent comprising a para-selective adsorbent. The adsorbent is preferably a para-selective, non-acidic, molecular sieve. The adsorbent is more preferably a para-selective, non-acidic, medium pore molecular sieve. The para-selective, non-acidic medium pore molecular sieve is preferably selected from the group of molecular sieve structure types consisting of MFI, TON, MTT, MEL, EUO, and FER. The molecular sieve is preferably of the MFI structure type and the process is preferably operated in the vapor phase at elevated temperatures and pressures wherein the temperature is substantially isothermal. The para-xylene which has been separated from a $C_8$ aromatic mixture using the above PSA process is then purified by simulated moving bed adsorption.

The process of the invention relates to a process for separating and recovering para-xylene from a gaseous mixture comprising $C_8$ aromatic hydrocarbons, the process comprising:

(a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream, and a para-xylene-rich effluent stream;

(b) sending at least a portion of the para-xylene-rich stream to a simulated moving bed adsorption unit and subjecting said para-xylene-rich stream to simulated moving bed adsorption to produce a para-xylene product stream and an ethylbenzene-rich $C_8$ aromatic stream;

(c) sending at least a portion of the meta-xylene and ortho-xylene-rich stream to an isomerization unit and isomerizing said stream to produce an isomerizate having an increased concentration of para-xylene;

(d) recycling at least a portion of the isomerizate from step (c) to step (a);

(e) removing any desorbent from the ethylbenzene-rich $C_8$ aromatic stream from step (b) and then contacting at least a portion of the ethylbenzene-rich $C_8$ aromatic stream with an ethylbenzene conversion catalyst and converting said stream to produce an effluent stream comprising mixed xylenes; and (f) recycling at least a portion of the effluent stream comprising mixed xylenes from step (e) to step (a).

Liquid-phase adsorption chromatography, also referred to as simulated moving bed adsorption chromatography (SiMBAC), is commercially licensed by UOP and IFP. Descriptions of SiMBAC processes and process conditions which would be suitable for integration with PSA in the process of the present invention are disclosed in U.S. Pat. Nos. 2,985,589; 3,201,491; 3,626,020; 3,696,107; 3,729,523; 4,039,599; 4,184,943; 4,381,419; 4,402,832, and U.S. Pat. No. 5,284,992, all of which are incorporated herein by reference in their entireties.). It is widely recognized that, next to the feedstock costs, the separation and purification portions comprise the most expensive component of the para-xylene production process. The present invention has the advantage of reducing such costs and providing a more efficient process for the production of para-xylene by virtue of using PSA to significantly reduce the amount of meta-xylene and ortho-xylene sent to a simulated moving bed liquid chromatographic section. In the discussion of the PSA component of the present invention below, the amounts of meta-xylene and ortho-xylene in the para-xylene or para-xylene and ethylbenzene effluent streams are reported as mole percent based on total $C_8$ aromatics. The amount of para-xylene or para-xylene and ethylbenzene in the meta-xylene and ortho-xylene effluent streams are also reported as mole percent based on total C8 aromatics. Those skilled in the art will recognize that, with regard to the concentration of pX, mX, oX, and/or EB in a given stream of C8 aromatics, mole percent equals weight percent.

The present invention also relates to a process for separating and recovering para-xylene from a gaseous mixture comprising $C_8$ aromatic hydrocarbons, the process comprising:

(a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;

(b) sending at least a portion of the para-xylene-rich stream to a simulated moving bed adsorption unit and subjecting said para-xylene-rich stream to simulated moving bed adsorption to produce a para-xylene product stream and an ethylbenzene-rich $C_8$ aromatic stream;

(c) sending at least a portion of the meta-xylene and ortho-xylene-rich stream to an isomerization unit and isomerizing said stream to produce an isomerizate having an increased concentration of para-xylene;

(d) recycling at least a portion of the isomerizate from step (c) to step (a);

(e) removing any desorbent from the ethylbenzene-rich $C_8$ aromatic stream from step (b) and then contacting at least a portion of the ethylbenzene-rich $C_8$ aromatic stream with an ethylbenzene conversion catalyst and converting at least a portion of the ethylbenzene in said stream to produce an effluent stream comprising mixed xylenes; and (f) recycling at least a portion of the effluent stream comprising mixed xylenes from step (e) to step (a).

In one embodiment of the process of the present invention, the gaseous mixture comprising meta-xylene, ortho-xylene, para-xylene, and ethylbenzene is contacted with an ethylbenzene conversion catalyst to remove at least a portion of the ethylbenzene prior to being subjected to pressure swing adsorption in step (a).

In one embodiment of the process of the present invention, at least a portion of the ethylbenzene-rich $C_8$ aromatic stream from step (b) is combined with the meta-xylene and ortho-xylene-rich effluent stream from step (a) and contacted with a xylene isomerization catalyst which is capable of isomerizing xylenes in a mixed $C_8$ aromatics feed and converting at least a portion of any ethylbenzene in the such $C_8$ aromatics feed to produce an effluent stream comprising mixed xylenes which is then recycled to step (a).

In accordance with the process of the invention, the isomerization catalyst reactor, where the xylenes are isomerized to equilibrium and where at least a portion of the ethylbenzene may be converted to xylenes or products which can be separated by fractional distillation from the $C_8$ aromatics, contains at least one catalyst that is capable of isomerizing xylenes in a mixed $C_8$ aromatic feed to produce an equilibrium mixture of xylenes and which may also possess the capability of converting at least a portion of any EB in such feed.

The isomerization catalyst and ethylbenzene conversion catalyst may be the same catalyst or may be two different catalysts.

The meta-xylene and ortho-xylene-rich effluent stream produced by PSA in step (a), and the ethylbenzene-rich $C_8$ aromatic stream produced by SiMBAC in step B, may be sent to the same catalyst reactor. The catalyst may be a dual function catalyst capable of isomerizing xylenes and converting ethylbenzene or it may be a dual catalyst system wherein one catalyst functions as the isomerization catalyst and the other catalyst functions as the ethylbenzene conversion catalyst. The catalysts may be in the same reactor or in different reactors. If the catalysts are in different reactors, the meta-xylene and ortho-xylene-rich effluent stream produced by PSA in step (a) is contacted with the isomerization catalyst to produce a stream comprising mixed xylenes having an enriched para-xylene content, and the ethylbenzene-rich $C_8$ aromatic stream produced by SiMBAC in step (b) is contacted with the ethylbenzene conversion catalyst to produce a stream comprising mixed xylenes.

In one embodiment of the invention, the ethylbenzene-rich $C_8$ aromatic stream produced by SiMBAC is collected as a product stream, and the ethylbenzene is recovered by methods well known in the art.

The PSA component of the process of the present invention relates to a method for separating para-xylene from a gaseous feed mixture containing meta-xylene and ortho-xylene under substantially isothermal conditions comprising:

(a) adsorbing the mixture onto an adsorbent containing a para-selective adsorbent capable of selectively adsorbing para-xylene at a temperature and pressure at which at least 0.01 grams of para-xylene may be adsorbed per gram of adsorbent;

(b) producing a first effluent stream containing a mixture of ortho-xylene and meta-xylene, having no more than a total of about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, more preferably no more than about 1 mole percent of para-xylene, and most preferably less than about 1 mole percent of para-xylene based on total $C_8$ aromatics;

(c) selectively removing feed from the non-selective void volume;

(d) selectively desorbing para-xylene by decreasing partial pressure of para-xylene; and (e) collecting a stream containing para-xylene and having no more than a total of about 50 mole percent of meta-xylene and ortho-xylene based on total $C_8$ aromatics; preferably less than about 50 mole percent of meta-xylene and ortho-xylene, more preferably no more than about 45 mole percent of meta-xylene and ortho-xylene, more preferably less than about 45 mole percent of meta-xylene and ortho-xylene, more preferably no more than about 40 mole percent of meta-xylene and ortho-xylene, preferably less than about 40 mole percent of meta-xylene and ortho-xylene, more preferably no more than about 35 mole percent of meta-xylene and ortho-xylene, more preferably less than about 35 mole percent of meta-xylene and ortho-xylene, more preferably no more than about 30 mole percent of meta-xylene and ortho-xylene, more preferably less than about 30 mole percent of meta-xylene and ortho-xylene, more preferably no more than about 25 mole percent of meta-xylene and ortho-xylene, more preferably less than about 25 mole percent of meta-xylene and ortho-xylene, more preferably no more than about 20 mole percent of meta-xylene and ortho-xylene xylene, more preferably less than about 20 mole percent of meta-xylene and ortho-xylene, more preferably no more than about 15 mole percent of meta-xylene and ortho-xylene, more preferably less than about 15 mole percent of meta-xylene and ortho-xylene, more preferably no more than about 10 mole percent of para-xylene, more preferably less than about 10 mole percent of meta-xylene and ortho-xylene, more preferably no more than about 5 mole percent of meta-xylene and ortho-xylene, and most preferably less than about 5 mole percent of meta-xylene and ortho-xylene based on total $C_8$ aromatics.

A practice of the invention involves principally proceeding by repeated cycles comprising in an individual cycle the above steps (a) through (e).

In step (a) of the PSA component of the process of the present invention described above, it is preferable that at least 0.01 g of para-xylene be adsorbed per gram of para-selective adsorbent contained in the adsorbent; more preferable that at least 0.02 g of para-xylene be adsorbed per gram of para-selective adsorbent contained in the adsorbent; and even more preferable that at least 0.03 g of para-xylene be adsorbed per gram of para-selective adsorbent contained in the adsorbent.

Preferably, the first effluent stream mixture of ortho-xylene and meta-xylene produced in the process of the invention, as, for example, in step (b) above, will contain no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene, and even more preferably less than about 1 mole percent of para-xylene.

Preferably, the para-xylene-containing stream collected in the process of the invention, as, for example, in step (e) above, will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

The molecular sieve is preferably a para-selective, non-acidic medium pore molecular sieve. Preferably, the molecular sieve comprises silicalite, and more preferably, the molecular sieve comprises orthorhombic crystals of silicalite having an average minimum dimension of at least about 0.2 μm.

In one embodiment of the invention, the adsorbent comprises a para-selective, adsorbent and a binder. The binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

A para-selective adsorbent is an adsorbent that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

A preferred para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

A more preferred para-selective adsorbent, when subjected to an equal molar mixture of $C_8$ aromatics at 50° C., will adsorb pX and EB preferentially over mX and oX, such that the total pX and EB in the adsorbate is at least about 80% relative to the total $C_8$ aromatics, even more preferably, at least about 85% relative to the total $C_8$ aromatics, still more preferably, at least about 90% relative to the total $C_8$ aromatics; and yet more preferably, at least about 95% relative to the total $C_8$ aromatics; and most preferably, at least about 97% relative to the total $C_8$ aromatics.

In the present invention the operating temperature is preferably from about 350° F. to about 750° F. and the operating pressure is preferably from about 30 psia to about 400 psia (from about 206 kPa to about 2760 kPa).

The PSA component of the process of the present invention additionally relates to a method to separate para-xylene and ethylbenzene from a gaseous feed mixture containing meta-xylene and ortho-xylene under substantially isothermal conditions comprising:

(a) adsorbing the mixture onto an adsorbent containing a para-selective adsorbent capable of selectively sorbing para-xylene and ethylbenzene at a temperature and pressure at which at least 0.01 grams of para-xylene and ethylbenzene may be adsorbed per gram of adsorbent;

(b) producing a first effluent stream containing a mixture of ortho-xylene and meta-xylene having no more than a total of about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, more preferably no more than about 1 mole percent of para-xylene and ethylbenzene, and most preferably less than about 1 mole percent of para-xylene and ethylbenzene based on total $C_8$ aromatics;

(c) selectively removing feed from the non-selective void volume;

(d) selectively desorbing para-xylene and ethylbenzene by decreasing partial pressure of para-xylene and ethylbenzene; and (e) collecting a stream containing para-xylene and ethylbenzene and having no more than a total of about 50 mole percent of meta-xylene and ortho-xylene based on total $C_8$ aromatics.

A practice of the invention involves principally proceeding by repeated cycles comprising in an individual cycle the above steps (a) through (e).

In a preferred embodiment of the above process, the effluent comprising meta-xylene and ortho-xylene collected in step (b) will be substantially free of ethylbenzene and para-xylene.

In a preferred embodiment of the above process, the second effluent product comprising ethylbenzene and para-xylene collected in step (e) will be substantially free of meta-xylene and ortho-xylene.

In step (a) of the PSA component of the process of the present invention described above, it is preferable that at least 0.01 g of para-xylene and ethylbenzene be adsorbed per gram of para-selective adsorbent contained in the adsorbent; more preferable that at least 0.02 g of para-xylene and ethylbenzene be adsorbed per gram of para-selective adsorbent contained in the adsorbent; still more preferable that at least 0.03 g of para-xylene and ethylbenzene be adsorbed per gram of para-selective adsorbent contained in the adsorbent.

The PSA component of the process of the present invention also relates to a process for separating a mixture of organic compounds having normal boiling points in a temperature range from about 80° C. to about 160° C., which process comprises:

(a) providing an adsorbent bed comprising a para-selective adsorbent which exhibits capacity to selectively adsorb and desorb para-xylene and ethylbenzene under substantially isothermal conditions of temperature at operating pressure, disposed in a vessel having at least one inlet and at least one outlet such that gas entering an inlet passes through the adsorbent bed to an outlet, and containing a purge gas substantially free of $C_8$ aromatic compounds;

(b) flowing a gaseous feed mixture comprising xylenes and ethylbenzene into the bed through one or more of the vessel inlets, and collecting an effluent from one or more of the outlets comprising purge gas substantially free of $C_8$ aromatic compounds while selectively adsorbing para-xylene and ethylbenzene from the gaseous mixture under substantially isothermal conditions in the bed;

(c) continuing the flow of gaseous feed and collecting from one or more of the outlets and segregating a second effluent comprising m-xylene and o-xylene having no more than about 25 mole percent of p-xylene and ethylbenzene;

(d) stopping the feed mixture flowing into the bed through one or more inlets just prior to breakthrough (i.e., the adsorption front is close to the exit end of the adsorbent column), and flowing purge gas preferably in a direction counter to the direction of the $C_8$ aromatic feed, while maintaining substantially isothermal conditions in the bed, and collecting from one or more of the outlets an effluent gaseous mixture of $C_8$ aromatic feed until effluent at the outlet contains no more than about 50 mole percent of meta-xylene and ortho-xylene;

(e) continuing the flow of purge gas and collecting from one or more of the outlets and segregating an effluent comprising ethylbenzene and p-xylene which contains no more than about 50 mole percent of meta-xylene and ortho-xylene; and (f) repeating steps (b) through (e).

In a preferred embodiment of the above process, the effluent comprising m-xylene and o-xylene collected in step (c) will be substantially free of para-xylene and ethyl benzene.

In a preferred embodiment of the above process, in step (d) the effluent gaseous mixture of $C_8$ aromatic feed will be collected until the effluent at the outlet is substantially free of meta-xylene and ortho-xylene.

In a preferred embodiment of the above process, the effluent comprising ethylbenzene and p-xylene collected in step (e) will be substantially free of meta-xylene and ortho-xylene.

A practice of the PSA component of the invention involves principally proceeding by repeated cycles comprising in an individual cycle the above steps (a) through (f).

In a preferred embodiment of the process, the flow of the purge gas is counter current to the flow of the gaseous feed mixture.

In one embodiment of the PSA component of the process of the invention, steps (b) through (e) are repeated with a cycle time of from about 2 minutes to about 200 minutes, preferably with a cycle time of from about 3 minutes to about 50 minutes, more preferably with a cycle time of from about 3 minutes to about 30 minutes.

In an embodiment of the PSA component of the process at least a portion of the effluent gaseous mixture collected in step (d) is admixed with the gaseous feed mixture in subsequent cycles.

In another embodiment of the PSA component of the process, the purge gas comprises hydrogen, and steps (b) through (e) are repeated with a cycle time of from about 3 minutes to about 30 minutes under substantially isothermal conditions at a temperature of about 350° F. to about 750° F. and at constant operating pressure at a pressure of at least about 30 psia.

An additional embodiment of the PSA component of the invention comprises a process for separating a mixture of ethylbenzene and the isomers of xylene, which process comprises:

(a) providing an adsorbent bed comprising para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(b) flowing a gaseous feed mixture comprising xylene isomers and ethylbenzene into the adsorbent bed through one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene while maintaining substantially isothermal conditions in the adsorbent bed and the flow of feed at the pressure for adsorption;

(d) replacing the feed mixture flowing into the bed though one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(e) reducing the pressure to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene.

In a preferred embodiment of the above PSA component process:

(a) the flow of said para-xylene and ethylbenzene purge gas is countercurrent to the flow of the gaseous feed mixture;

(b) the para-xylene and ethylbenzene effluent flow during depressurization is countercurrent to the flow of the gaseous feed mixture; and (c) the flow of meta-xylene and ortho-xylene to pressurize the vessel is countercurrent to the feed gas flow.

In a preferred embodiment of the above PSA component process, the effluent comprising meta-xylene and ortho-xylene collected in step (c) will be substantially free of ethylbenzene and para-xylene.

In a preferred embodiment of the above PSA component process, the second effluent product comprising ethylbenzene and para-xylene collected in step (f) will be substantially free of meta-xylene and ortho-xylene.

A further embodiment of the PSA component of the invention comprises a process for separating a mixture of ethylbenzene and the isomers of xylene, which process comprises:

(a) providing at least two adsorbent beds containing a para-selective adsorbent which exhibits capacity to selectively adsorb and desorb para-xylene and ethylbenzene under substantially isothermal conditions at operating pressure, disposed in sequentially connected or interconnected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(b) flowing a gaseous feed mixture comprising xylene isomers and ethylbenzene into the adsorbent bed in the first vessel though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene while maintaining substantially isothermal conditions in the adsorbent bed and the flow of feed at the pressure for adsorption;

(d) stopping the flow of feed and reducing the pressure in the first vessel sufficiently to permit removal of at least a portion of the feed from non-selective voids while maintaining substantially isothermal conditions in the bed by equalizing the pressure in the first vessel with the pressure in the second vessel which is at a lower pressure;

(e) further reducing the pressure in the first vessel to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene.

In a preferred embodiment of the above PSA component process, the effluent comprising meta-xylene and ortho-xylene collected in step (c) will be substantially free of ethylbenzene and para-xylene.

In a preferred embodiment of the above PSA component process, the second effluent product comprising ethylbenzene and para-xylene collected in step (f) will be substantially free of meta-xylene and ortho-xylene.

In the above PSA component process, following step (f), a purge gas comprising meta-xylene and ortho-xylene can be added to the first vessel to displace para-xylene and ethylbenzene in the non-selective voids, and an effluent comprising the para-xylene and ethylbenzene is collected.

Another embodiment of the PSA component of the present invention comprises a process for separating a mixture of ethylbenzene and the isomers of xylene, which process comprises:

(a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture of substantially meta-xylene and ortho-xylene to a preselected pressure for adsorption;

(b) flowing a gaseous feed mixture comprising xylene isomers and ethylbenzene into the adsorbent bed though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene xylene which contains no more than a total of about 25 mole percent of ethylbenzene and para-xylene while maintaining substantially isothermal conditions in the adsorbent bed and the flow of feed at the pressure for adsorption;

(d) stopping the flow of feed and reducing operating pressure to a pressure at which para-xylene and ethylbenzene desorb while maintaining substantially isothermal conditions in the bed; and (e) collecting a second effluent product comprising ethylbenzene and para-xylene which contains no more than a total of about 50 mole percent of meta-xylene and ortho-xylene.

In the above embodiment, preferably, following step (e), a purge gas comprising meta-xylene and ortho-xylene is added to the first vessel to displace para-xylene and ethylbenzene in the non-selective voids, and an effluent comprising the para-xylene and ethylbenzene is collected.

In a preferred embodiment of the above PSA component process, the effluent comprising meta-xylene and ortho-xylene collected in step (c) will be substantially free of ethylbenzene and para-xylene.

In a preferred embodiment of the above PSA component process, the second effluent product comprising ethylbenzene and para-xylene collected in step (e) will be substantially free of meta-xylene and ortho-xylene.

In the embodiments of the pressure swing adsorption (PSA) component of the process of the present invention described above, it is preferred that the first effluent stream mixture of ortho-xylene and meta-xylene produced in the PSA process component of the invention will contain no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene.

In the embodiments of the pressure swing adsorption (PSA) component of the process of the present invention described above wherein the first effluent mX/oX stream contains both para-xylene and ethylbenzene, it is preferred that the first effluent stream mixture of ortho-xylene and meta-xylene produced in the process of the invention will contain no more than about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, and still more preferably no more than about 1 mole percent of para-xylene and ethylbenzene.

In the embodiments of the pressure swing adsorption (PSA) component of the process of the present invention described above, it is preferred that the para-xylene-containing stream collected in the process of the invention will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the pressure swing adsorption (PSA) component of the process of the present invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

A purge gas substantially free of $C_8$ aromatic compounds will contain no more than about 10 wt %, and preferably less than about 5 wt %, and most preferably less than about 2 wt % of $C_8$ aromatic compounds.

A fraction or stream substantially free of p-xylene and ethylbenzene will contain no more than a total of about 5 mole percent of p-xylene and ethylbenzene based on total $C_8$ aromatics.

A fraction or stream substantially free of para-xylene will contain no more than about 5 mole percent of para-xylene based on total $C_8$ aromatics. Preferably such a fraction will contain no more than about 1 mole percent of para-xylene based on total $C_8$ aromatics.

For those process steps conducted at constant pressure, those skilled in the art will recognize that during operation there may be slight variations in pressure due to pressure drops across the system or changes in flows; however the pressure will remain substantially constant.

A fraction or stream substantially free of m-xylene and o-xylene will contain no more than a total of about 25 mole percent of m-xylene and o-xylene based on total $C_8$ aromatics. Preferably such a stream will contain no more than about 20 mole percent, more preferably no more than about 15 mole percent; still more preferably no more than about 10 mole percent; and most preferably no more than about 5 mole percent of m-xylene and o-xylene based on total $C_8$ aromatics.

The present invention also relates to a method of pressure swing adsorption which includes a plurality of steps and which provides recovery from a mixture comprising $C_8$ aromatics of a product stream of p-xylene or p-xylene and ethylbenzene which is substantially free of m-xylene and o-xylene as well as a product stream of meta-xylene and ortho-xylene which is substantially free of p-xylene and ethylbenzene. The present invention provides a pressure swing adsorption process whereby there can be obtained from a feed comprising $C_8$ aromatics a high yield of a high purity product stream of p-xylene and ethylbenzene and also a high yield of a high purity product stream of m-xylene and o-xylene. The para-xylene/ethylbenzene stream can then be subjected to simulated moving bed adsorption to produce higher yields of para-xylene product at lower capital and energy cost.

DESCRIPTION OF THE PREFERRED EMBODIMENTS

Figure 1:
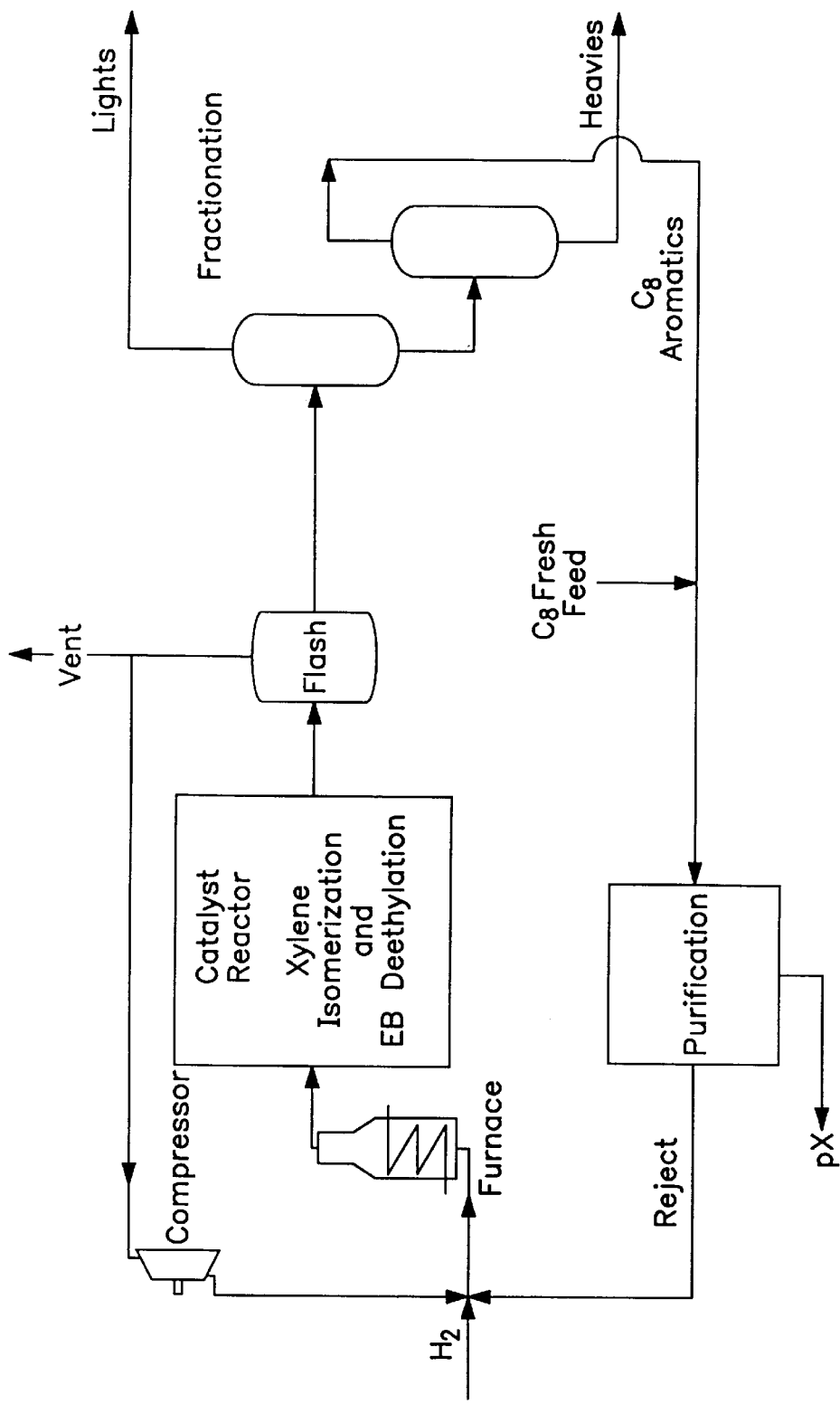
FIG. 1 is a schematic representation of the known combination of an isomerization catalyst reactor and a crystallization unit.

The present invention is a process for producing para-xylene from a $C_8$ aromatics feed which integrates pressure swing adsorption and simulated moving bed (liquid chromatography) purification. The present invention includes a pressure swing adsorption (PSA) process component for separating para-xylene and ethylbenzene from mixed $C_8$ aromatics using a para-selective adsorbent, which is preferably a non-acidic, medium pore molecular sieve, and a simulated moving bed (liquid chromatography) (SiMBAC) purification component for purifying the para-xylene or para-xylene/ethylbenzene effluent stream from the PSA component. A portion of the meta-xylene and ortho-xylene effluent which is also produced in the PSA process component may be sent to an isomerization unit and isomerized to produce an isomerizate comprising an equilibrium mixture of xylenes. The effluent from the simulated moving bed adsorption component, which comprises an ethylbenzene-rich $C_8$ aromatic stream and desorbent from the SiMBAC process can be distilled to remove any desorbent from the ethylbenzene-rich $C_8$ aromatic stream and then at least a portion of the ethylbenzene-rich $C_8$ aromatic stream can be sent to an isomerization unit and contacted with an isomerization catalyst or an isomerization/ethylbenzene conversion catalyst to produce an isomerizate comprising a mixture of xylenes.

PSA Component

The PSA component of the present invention uses selective adsorption, selective desorption and displacement at substantially isothermal temperatures to provide a substantially pure product stream of para-xylene and ethylbenzene and a substantially pure stream of ortho-xylene and meta-xylene. The components in these streams can be further separated to provide substantially pure para-xylene, ethylbenzene, ortho-xylene, and meta-xylene products by methods known in the art.

In the process of the present invention the para-selective adsorbent preferably comprises a para-selective, non-acidic molecular sieve, more preferably a para-selective, non-acidic, medium pore molecular sieve, and more preferably, silicalite. Most preferably, the molecular sieve comprises orthorhombic crystals of silicalite having an average minimum dimension of at least about 0.2 $\mu$m.

A para-selective adsorbent is an adsorbent that, when subjected to an equal molar mixture of xylenes at 122° F. (50° C.), adsorbs para-xylene preferentially over meta-xylene and ortho-xylene, such that the total para-xylene in the adsorbate is at least about 75% relative to the total $C_8$ aromatics, preferably greater than 75% relative to the total $C_8$ aromatics; more preferably, at least about 80% relative to the total $C_8$ aromatics; even more preferably, at least about 85% relative to the total $C_8$ aromatics; still more preferably, at least about 90% relative to the total $C_8$ aromatics; and yet more preferably, at least about 95% relative to the total $C_8$ aromatics; and most preferably, at least about 97% relative to the total $C_8$ aromatics.

The adsorbent used in the process of the present invention may comprise a para-selective adsorbent and a binder, more preferably a para-selective, non-acidic medium pore molecular sieve and a binder. When a para-selective adsorbent and binder are used as the adsorbent, the binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

Preferably, the adsorbent will contain about 5 to about 100 weight percent para-selective adsorbent.

In the process of the present invention, it is preferred that at least 0.01 grams of para-xylene is adsorbed per gram of molecular sieve, more preferable that at least 0.02 grams of para-xylene is adsorbed per gram of molecular sieve, and most preferable that at least 0.03 grams of para-xylene is adsorbed per gram of molecular sieve.

The process of the present invention, is operated at a temperature and pressure sufficient to give rapid adsorption and desorption of para-xylene and/or ethylbenzene. The temperature and pressure conditions are chosen to be able to achieve rapid adsorption/desorption rates and may vary depending upon the particular adsorbent used. Suitable temperature may be selected in ranges of above about 350° F. (176° C.), preferably above about 400° F. (200° C.), and more preferably above about 450° F. (230° C.).

Suitable pressures may be selected in ranges of above about 30 psia (206 kPa), above about 50 psia (345 kPa), and above about 100 psia (2760 kPa) with pressures preferably above about 50 psia (345 kPa).

Those skilled in the art will recognize that suitable operating temperatures and pressures for achieving sufficiently rapid adsorption and desorption for in the PSA process may vary. For example the temperature and pressure may be in the ranges of about 350° F. (176° C.) to about 750° F. (400° C.) and about 30 psia (206 kPa), to about 400 psia (2760 kPa); more preferably about 400° F. (200° C.) to about 650° F. (350° C.) and about 50 psia (345 kPa) to about 300 psia (2070 kPa); more preferably about 450° F. (225° C.) to about 600° F. (300° C.) and about 50 psia (345 kPa) to about 250 psia (1380 kPa).

In the PSA process of the present invention, the operating temperature is typically at least about 350° F. (176° C.), preferably at least about 400° F. (200° C.) more preferably at least about 450° F. (230° C.), more preferably at least about 500° F. (260° C.), more preferably at least about 550° F. (285° C.). For some embodiments, the temperature may be at least about 600° F. (315° C.). The operating temperature may range from about 350° F. (176° C.) to about 750° F. (400° C.) preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (370° C.).

In the process of the present invention, the operating pressure is at least about 30 psia (206 kPa), preferably at least about 50 psia (345 kPa) and may range from about 50 psia (345 kPa) to about 400 psia (2760 kPa). The operating pressure will preferably range from about 30 psia to about 400 psia, more preferably from about 50 psia to about 400 psia, more preferably from about 100 psia to about 400 psia (from about 690 kPa to about 2760 kPa), more preferably from about 150 psia to about 350 psia (from about 1030 kPa to about 2410 kPa). For some embodiments, the pressure may range from about 200 psia to about 300 psia (from about 1380 kPa to about 2070 kPa).

The term "substantially isothermal" means that the only change in temperature of the adsorbent during the PSA cycle is due to the heats of adsorption and desorption.

References to "substantially constant pressure" or "substantially constant operating pressure", mean that during the process referred to there is no depressurization of the adsorption vessel so that it remains at constant pressure; however, those skilled in the art will recognize that there may be some slight variation in pressure due to changes in flows or that the partial pressure of the adsorbed phase may be reduced by an inert purge gas.

A "substantially pure product stream of para-xylene and ethylbenzene" means a stream containing para-xylene and ethylbenzene with less than a total of 25 mole percent, and preferably less than 10 mole percent, and most preferably less than 5 mole percent meta-xylene and ortho-xylene based on total $C_8$ aromatics.

A "substantially pure product stream of ortho-xylene and meta-xylene" means a stream containing ortho-xylene and meta-xylene with less than a total of 5 mole percent, and preferably less than 1 mole percent of para-xylene and ethylbenzene based on total $C_8$ aromatics.

The present invention relates to a pressure swing adsorption process for separation of para-xylene (pX) and ethylbenzene (EB) from mixed $C_8$ aromatics using a para-selective adsorbent. For the purpose of this invention, a para-selective adsorbent is defined as a material that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

Preferably, a para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

The preferred adsorbent is a non-acidic molecular sieve of the MFI structure type (same structure as the acidic zeolite ZSM-5 but with the acid sites replaced with neutral moieties so that the molecular sieve is non-catalytic and does not isomerize xylenes). A particularly preferred adsorbent is silicalite. The process is operated in the vapor phase at elevated temperatures and pressures. The pX and EB are substantially adsorbed at high partial pressures while meta-xylene (mX) and ortho-xylene (OX) are not substantially adsorbed. A fixed bed of adsorbent is saturated with pX and EB, wherein the feed to the process is stopped, and then lowering the partial pressure desorbs the pX and EB. The process effluent is rich in pX and EB.

The pressure swing adsorption process is preferably a fixed-bed, batch-wise isothermal process for separation of pX and EB from mX and oX. The separation is based on the selective adsorption of pX and EB into a para-selective adsorbent, such as orthorhombic silicalite crystals having an average minimum dimension of around 0.2 μm or greater, at high pressure and desorption at low pressure. At high pressure, pX and EB are adsorbed, while mX and oX pass through the bed and are essentially not adsorbed producing a substantially pure stream of mX and oX which contains only minor amounts of other substances. The mX and oX may be collected at the outlet of the bed and recycled to an isomerization catalyst to produce more pX or a portion or all may be further separated to produce pure mX and/or pure oX. After saturation of the adsorbent the feed is discontinued and the pX and EB are desorbed by lowering the xylene partial pressure. By operating in the vapor phase at high temperatures, preferably greater than about 350° F. (176° C.) the rates of both adsorption and desorption are fast, minimizing cycle time and reducing the amount of adsorbent and capital expense required for the separation. Use of a non-acidic zeolite or molecular sieve, such as silicalite, eliminates undesirable catalytic reactions of the adsorbed EB and pX, and avoids adsorption of olefins contaminants which reduce the adsorption capacity of the adsorbent.

In the present invention a preferred adsorbent is silicalite molecular sieve, comprising orthorhombic crystals having an average minimum dimension of around 0.2 μm or greater, which has high para-xylene and ethylbenzene selectivity. The para-xylene adsorption capacity of the silicalite adsorbent is from about 1 to about 15 wt %. at saturation. Adsorbent capacity is typically defined as grams adsorbate (i.e., material adsorbed) divided by grams adsorbent and can also be expressed as a weight percent by multiplying by 100. The process is conducted in the gas phase at a temperature of from about 350° F. to about 750° F. (about 176° C. to about 400° C.) and the unit pressure is about 30 psia to about 400 psia (about 206 kPa to about 2760 kPa).

The present invention is a pressure swing adsorption process for separation of pX and EB from mixtures of $C_8$ aromatics using a non-acidic, para-selective adsorbent, such as silicalite molecular sieve, comprising orthorhombic crystals having an average minimum dimension of around 0.2 μm or greater. During adsorption, mX and oX are substantially not adsorbed, while pX and EB are substantially adsorbed. The process will preferably operate at about 500° F. to about 750° F. (about 260 to about 400° C.) with pX partial pressures of about 30 to about 150 psi (about 200 to about 1000 kPa), preferably about 40 to about 120 psi (about 265 to about 800 kPa). Selective adsorption of pX and EB (from a feed containing pX, EB, mX and oX) occurs with a silicalite adsorbent, comprising orthorhombic crystals having an average minimum dimension of around 0.2 μm or greater. At elevated temperatures [greater than about 350° F. (176° C.)], adsorption of pX or pX/EB is effected at high partial pressures [greater than about 25 psi (about 170 kPa) partial pressure)]. Subsequently, rapid desorption without catalytic reaction is effected by lowering the partial pressure of the adsorbates. The partial pressure may be decreased by lowering the total pressure in the adsorption vessel or by purging the bed with an inert flow, for example, He, $N_2$, $H_2$, $CH_4$, $CO_2$ etc., while maintaining the unit pressure. The purge gas first displaces the $C_8$ aromatic feed from the non-selective void volume which lowers the partial pressure of para-xylene and ethylbenzene in the adsorption vessel and then sweeps out the adsorbate (substantially para-xylene and ethylbenzene) as it desorbs from the molecular sieve pores.

The present invention is a process for separation of para-xylene (pX) and ethylbenzene (EB) from meta-xylene (mX) and ortho-xylene (oX). The separation is based on selective adsorption of pX and EB into a non-acidic, silica molecular sieve, having structure type MFI (said material is commonly referred to as silicalite), comprising orthorhombic crystals having an average minimum dimension of around 0.2 μm or greater, at a higher partial pressure, followed by selective desorption (i.e., no isomerization upon desorption) at a lower partial pressure. The process is operated in a batchwise mode by first passing a stream containing a mixture of EB, pX, mX and oX over a fixed bed of silicalite. At high xylene partial pressure, pX and EB are substantially adsorbed, while mX and oX pass through the bed and are substantially not adsorbed. The mX and oX are collected at the outlet of the bed during the adsorption of pX and EB. After saturation of the silicalite, the feed is discontinued and the pX and EB are desorbed by lowering the xylene partial pressure. By operating in the vapor phase at high temperatures [greater than 350° F. (176° C.)], the rates of both adsorption and desorption are fast minimizing cycle time and reducing the amount of silicalite required for separation. Use of a non-acidic molecular sieve, such as silicalite eliminates undesirable catalytic reactions of the adsorbed EB and pX which occur with H-ZSM-5. Furthermore, non-acidic silicalite is less subject to adsorption of olefin contaminants, which reduce the adsorption capacity of H-ZSM-5.

Non-acidic molecular sieves of the MEL structure type are microporous materials having similar pore size and adsorption capacity to MFI molecular sieves, and as such would be expected to behave similarly. Both MFI and MEL molecular sieves are classified as medium pore molecular sieves. Other medium pore molecular sieves that may find use in the present invention are structure types MTW (12 ring structure, e.g., ZSM-12), ATO (12 ring structure, e.g., ALPO-31), NES (10 ring structure, e.g., Nu-87), TON (10 ring structure, e.g., Theta-1, ZSM-22), MTT (10 ring structure, e.g., ZSM-23), MFS (10 ring structure, e.g., ZSM-57), FER (10 ring structure), EUO (10 ring structure) AEL (10 ring structure, e.g., ALPO-11), AFO (10 ring structure, e.g., ALPO-41), and SUZ-4 (10 ring structure).

Large pore molecular sieves, such as mordenite, zeolite Beta, and faujasites, and amorphous adsorbents, such as silica, alumina, and clays, are non-selective, and therefore undesirable for use in the present invention, while small pore zeolites, such as zeolite A, are too small to admit pX and EB into the pores.

The adsorbent can be contained in one or more containers or vessels in which separation of a substantially pure stream of mX/oX and a substantially pure stream of pX/EB is effected using programmed flow into and out of the container or vessel. The separation of components taking place in the adsorbent column is a pressure swing adsorption separation wherein the cycle time is defined as the interval of time starting when feed is admitted into the vessel and ending at the time the vessel has been repressurized (i.e., when it is ready for the next addition of feed). Therefore, the cycle time can be described as the time interval at which feed is introduced to the pressurized adsorbent vessel, e.g., every 1 minute, every 5 minutes, every 10 minutes, every 15 minutes, etc. The "cycle" is the complete PSA process (i.e., summation of all the stages). Stages are usually discrete steps in the overall process, such as Feed, Blowdown, Purge, Repressurization; Feed Pressure Equalization, Blowdown, Purge, Repressurization; or Feed, Rinse, Blowdown, Repressurization, etc. However, in some cases the designation of stages can be more arbitrary, such as in the case of a process at constant pressure using a purge gas such as $CH_4$, $CO_2$, He, $H_2$ or $N_2$.

Effluent from the column during each cycle is separated into fractions, or cuts, which may include, for example, (1) a front end cut comprising the unadsorbed components, substantially oX and mX, (2) an intermediate cut comprising a mixture of $C_8$ aromatics where the pX content is greater than the pX content of the feed [i.e., wt % pX (intermediate) >wt % pX (feed)], and (3) a cut comprising the adsorbed components, which is substantially pure pX and EB.

The pressure swing adsorption process is carried out in the vapor phase. Preferred conditions for the process include temperatures from about 450° F. (230° C.) to about 750° F. (400° C.), preferably from about 500° F. (250° C.) to about 750° F. (400° C.), more preferably, from about 600° F. (315° C.) to about 700° F. (370° C.), sufficient to maintain components in the vapor phase at system pressures from about 100 psi (690 kPa) to about 400 psi (2760 kPa), preferably from about 150 psi (1030 kPa) to about 350 psi (2410 kPa), more preferably, from about 200 psi (1380 kPa) to about 300 psi (2070 kPa). The process is conducted at a substantially isothermal temperature.

The pressure swing adsorption (PSA) of the present invention may be conducted in staged cycles. One embodiment of the invention comprises a pressure swing adsorption cycle in which the pressure of the adsorbent vessel is substantially the same throughout the PSA cycle, and removal of the feed from the non-selective void volume and subsequent desorption of pX/EB is accomplished with a gas purge, such as methane hydrogen, nitrogen, or helium. Another embodiment of the invention comprises a four-stage PSA cycle in which a rinse stream of substantially pX/EB is used to displace feed from the non-selective void volume prior to desorption of pX/EB via lowering the absolute pressure of the adsorbent vessel.

A third embodiment of the invention comprises a four-stage PSA cycle in which pX/EB is desorbed by lowering the absolute pressure of the adsorbent vessel, and then is subsequently displaced from the non-selective void volume by a purge stream of substantially mX/oX.

A fourth embodiment of the invention comprises a PSA cycle similar to the third embodiment, with the exception that depressurization occurs in at least two steps, such that gas from depressurization is used to pressurize a regenerated bed (i.e., the cycle contains at least one pressure equalization step).

A fifth embodiment of the invention comprises a PSA cycle employing pressure equalization, a pX/EB rinse step prior to desorption of pX/EB by depressurization, and an mX/oX purge step.

In describing the preferred embodiments of the invention which are illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

Pressure Swing Adsorption Cycle for pX/EB Separation

The pressure swing adsorption component of the process of the present invention is preferably a fixed-bed, batch-wise substantially isothermal process which can be used to separate para-xylene (pX) and ethylbenzene (EB) from meta-xylene (mX) and ortho-xylene (oX). The separation is based on molecular size and consists of the selective adsorption of the smaller $C_8$ aromatics (pX and EB) into a para-selective adsorbent preferably a non-acidic, para-selective molecular sieve, such as silicalite, comprising orthorhombic crystals having an average minimum dimension of about 0.2 $\mu$m or greater, while mX and oX pass through the bed and are not adsorbed. The key to a viable commercial process (fast cycles, minimal adsorbent and capital) is operating at a temperature where the desorption rate is high, and consequently, at a pressure giving sufficient adsorption at that temperature. Thus, in the process of the invention, adsorption occurs at high pressure and high temperature; whereas, desorption occurs at low pressure and high temperature. The mX/oX stream may be recycled to the isomerization catalyst producing more pX or it may be further separated to obtain mX and/or oX. The pX/EB stream (rich in pX) may be purified via SiMBAC to give para-xylene having a purity of 99% or greater. Process Specifics:

Temperature Range: The temperature range of the PSA process used in the invention is preferably from about 350° F. to about 750° F. (about 176° C. to about 400° C.), preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (about (285° C. to about 370° C.).

The pressure swing adsorption cycle is preferably conducted under substantially isothermal conditions in which the only change in temperature of the adsorbent during the PSA cycle is due to the heats of adsorption and desorption.

High Pressure Side: About 30 to about 420 psia.

Pressure Ratio (High Pressure/Low Pressure): 2–30.

Adsorbent Capacity: About 1 to about 15 wt % at saturation.

The adsorbent may maintain adsorption capacity through many cycles which reduces the need to replace or recondition the adsorbent. This is another cost saving advantage of the process of the present invention.

PSA Process Cycle Designs

In the descriptions that follow pX/EB comprises para-xylene and ethylbenzene and represents the adsorbed phase, which is principally pX and EB, but could also contain other adsorbable components such as benzene, toluene, 1,4-methylethylbenzene, 1,4-diethylbenzene, linear paraffins (typically $C_9$) and mono-methylbranched paraffins (also typically $C_9$). Likewise, mX/oX comprises meta-xylene and ortho-xylene and represents the non-adsorbed phase which is principally mX and oX, but could also contain other non-adsorbable components such as trimethylbenzenes, other isomers of methylethylbenzene and diethylbenzene, cycloparaffins (typically $C_9$) and other sterically bulky components in the feed.

For each embodiment, one complete cycle is described. It is to be understood that practice of the invention involves principally proceeding by repeated said cycles. In the descriptions of the embodiments of the invention, the molecular sieve adsorbent may be referred to as a zeolite; however, it is to be understood that any suitable non-acidic, medium pore molecular sieve may be used as the adsorbent.

The preferred embodiments of the PSA component of the process of the present invention are described below.

PSA Embodiment 1: Desorption with Inert Gas Purge, e.g., $CH_4$, $CO_2$, $H_2$, $N_2$, He (FIG. 4)

Figure 4:
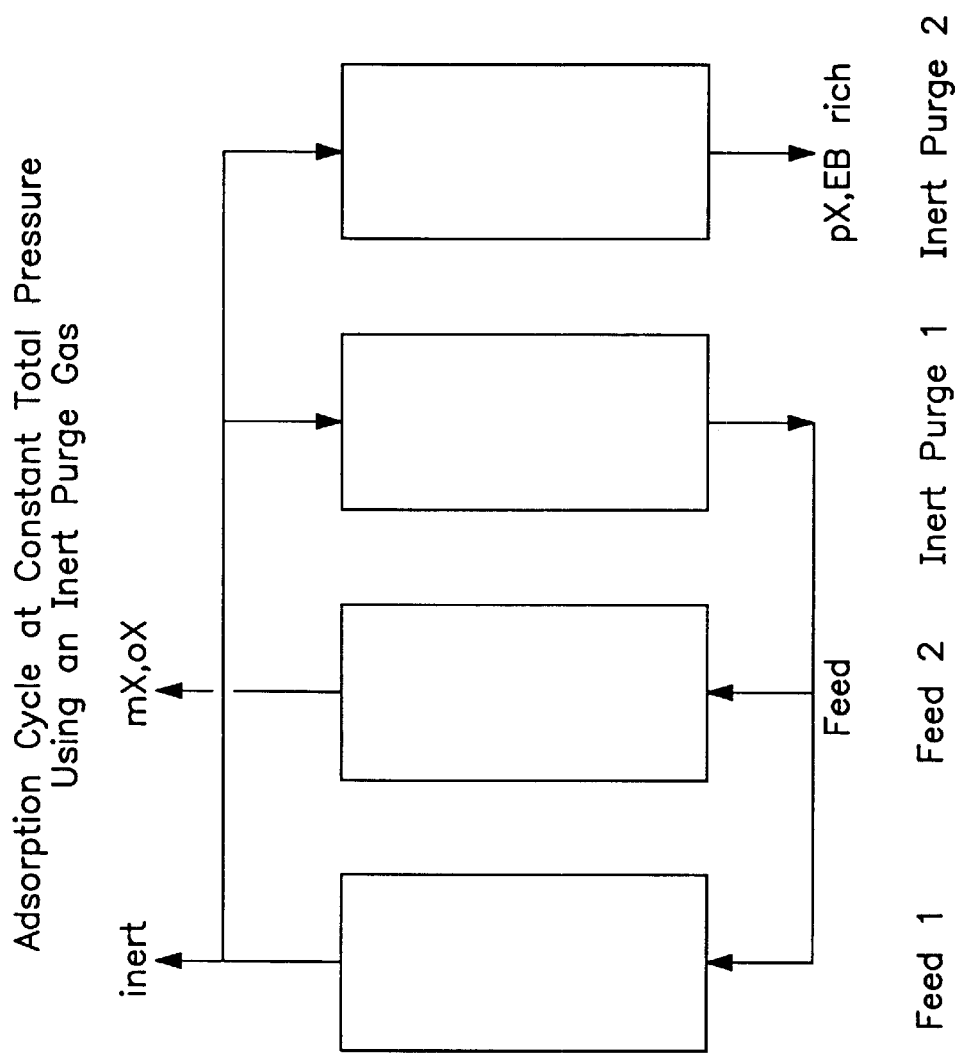
FIG. 4 is a schematic representing an adsorption cycle for pX/EB separation which operates at substantially constant system pressure and uses an inert gas purge, such as, for example, $CH_4$, $CO_2H_2$, $N_2$, or He, to accomplish desorption.

This embodiment is illustrated in FIG. 4. A typical bed of molecular sieve adsorbent contains about 20–30% of its volume in molecular sieve pores which selectively adsorb pX and EB and 80–70% of void space and large non-selective pores. This embodiment comprises a gas-phase process wherein the temperature is substantially isothermal and the total pressure is substantially constant. The pressure and temperature are selected to allow for rapid adsorption and desorption leading to rapid loading and unloading of the adsorbent bed. Cycle times may be from about 1 to about 30 minutes and are preferably no more than about 25 minutes, more preferably no more than about 20 minutes, still more preferably about 5 to about 15 minutes and most preferably, about 3 to about 15 minutes. Thus a preferred cycle time might be 3, 4, 5, 6, 7, 8, 9, 10, 11, 12, 13, 14, or, 15 minutes. Shorter cycle times are preferred since they reduce the amount of adsorbent and capital required.

Stage 1: Adsorption 1-Displacement of Purge Gas from the Void Space and Initial Adsorption of PX and EB Prior to admitting $C_8$ aromatic feed flow into the adsorbent vessel, the bed is essentially free of $C_8$ aromatics and contains the purge gas. Feed containing a mixture of substantially $C_8$ aromatics (mX, oX, pX, EB), which can also contain some paraffins and naphthenes, $C_9$+ aromatics, benzene and toluene, is passed into the adsorption vessel where pX and EB are adsorbed into the pores of the molecular sieve leaving mX and oX in the void space. As the feed flow continues into the vessel, purge gas is displaced at the outlet of the reactor and recycled to the process.

This stage continues until the purge gas is essentially displaced from the void fraction. (Purge gas may remain in a portion of the molecular sieve pores.) Just prior to hydrocarbon breakthrough, purge gas recovery is discontinued.

Stage 2: Adsorption 2 (Product Collection of mX and oX and Saturation of the Molecular Sieve Pores with pX and EB)

With the removal of purge gas from the void volume, mX and oX exit from the outlet of the adsorption bed as the feed continues to enter the adsorption bed. This mX/oX effluent stream which is substantially free of pX and EB may be collected as one of the product streams for further purification of mX and oX or may be sent to a catalyst reactor for isomerization to an equilibrium xylene mixture.

Throughout this stage pX and EB continue to adsorb into the molecular sieve and mX and oX are displaced from the void fraction by incoming feed. At the end of the stage the void fraction contains feed and the molecular sieve pores contains pX and EB. Collection of the mX and oX is discontinued just prior to breakthrough of the feed.

Stage 3: (Desorption of the Feed from the Void Fraction)

During the two desorption steps, feed is discontinued and purge gas flows in to the adsorption vessel, typically countercurrent to the flow of $C_8$ aromatics during the feed step. Because the pX and EB are more strongly adsorbed inside the pores of the molecular sieve than the feed in the void fraction, the feed is more readily displaced by the purge gas. As purge gas enters the reactor the feed in the void fraction is removed at the reactor outlet along with a small amount of pX and EB displaced from the molecular sieve. The feed from this stage may be mixed with make-up feed or sent directly to another vessel which is in one of the adsorption stages. Stage 3 is complete when essentially all of the mX and oX have been purged from the vessel.

Stage 4: Collection of pX and EB

Once the feed is displaced from the void fraction, the effluent is highly concentrated in pX and EB. Since the purge gas lowers the partial pressure of pX and EB in the adsorbent vessel, pX and EB continue to desorb from the molecular sieve and exit the adsorbent vessel. This stream is collected for further purification of pX and EB. At the end of this stage the void fraction and molecular sieve pores are essentially filled with purge gas and the system is ready to admit feed flow and begin Stage 1 again.

Figure 3:
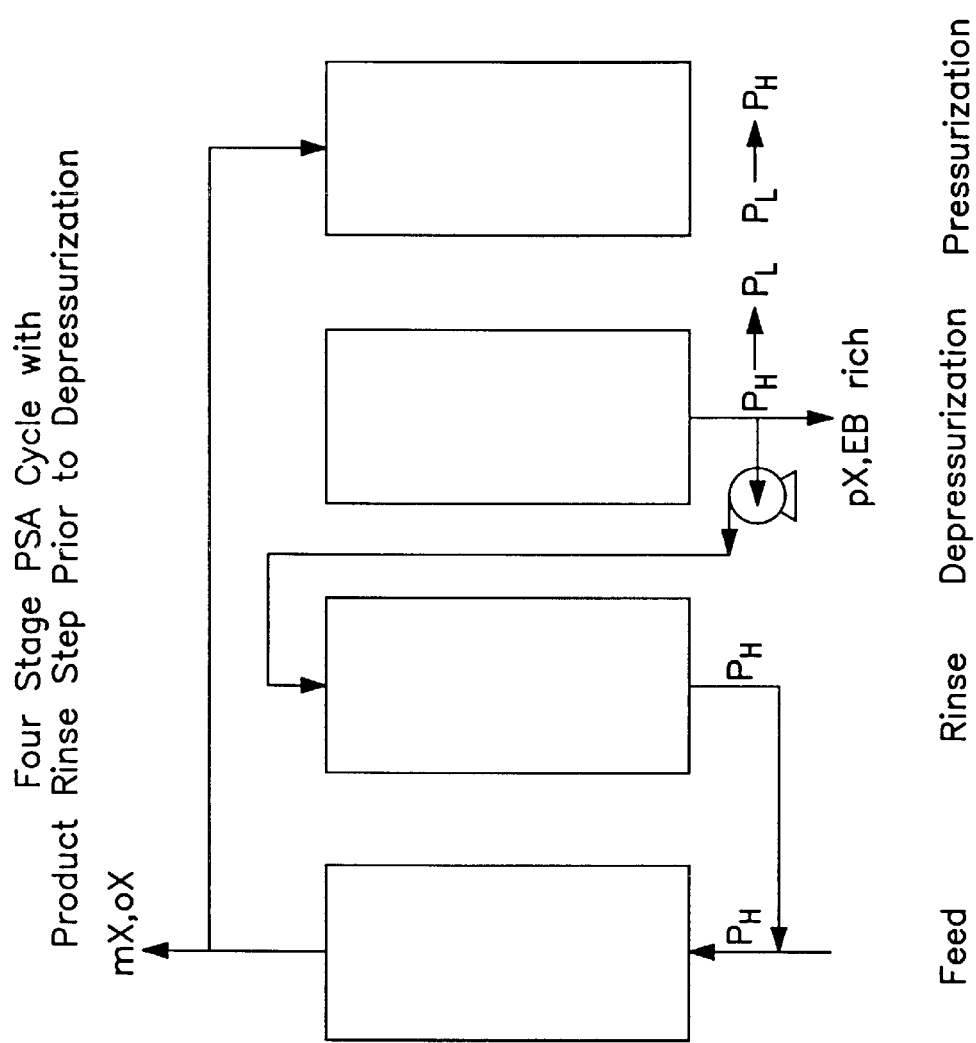
FIG. 3 is a schematic representing a four-stage pressure swing adsorption cycle for pX/EB separation in which a rinse stream of substantially pX/EB is used to displace feed from the non-selective void volume, prior to desorption via lowering of the absolute pressure.

PSA Embodiment 2: PX/EB Rinse Prior to Desorption by Depressurization (FIG. 3)

This process flow is similar to the process embodiment described above except that no $H_2$ (or $CH_4$, $CO_2$ He, $N_2$, etc.) is used during the desorption stages. Rather, removal of the feed from the void fraction is accomplished by rinsing with a stream of substantially pX/EB, and then pX/EB is desorbed from the adsorbent and recovered by depressurizing the adsorption vessel. Again this is a substantially isothermal, gas-phase process with cycle times of about 3 to about 15 min.

Stage 1: Adsorption of pX and EB

Prior to the introduction of $C_8$ aromatic feed, the molecular sieve pore volume is essentially free of pX/EB and the non-selective void volume (i.e., large meso-pores in the adsorbent, interstitial space between adsorbent particles, void space in the adsorbent vessel) is filled with substantially mX/oX. A feed containing substantially $C_8$ aromatics (mX, oX, pX, EB, which can also contain some paraffins and naphthenes, $C_9+$ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This is the end of the first stage and introduction of feed is stopped just prior to breakthrough.

Stage 2: Displacement of the Feed From the Non-Selective Void Volume

At the end of the first stage, the molecular sieve pores are filled with pX/EB and the non-selective void volume is filled with feed. In order to increase the recovery and purity of pX/EB during the depressurization step, the feed is displaced from the non-selective void space by the addition of a high pressure stream containing substantially pX/EB flowing countercurrent to the $C_8$ aromatic flow during the feed step. The feed displaced during this stage may be sent to another adsorption vessel in Stage 1 of the cycle. Once the feed has been displaced and the non-selective void volume filled with pX/EB, the addition of pX/EB is stopped just prior to pX/EB breakthrough and Stage 2 is complete.

Stage 3: Collection of PX and EB

Once the feed is displaced from the void fraction, the vessel pressure is lowered resulting in desorption of the pX, EB from the molecular sieve. Effluent flow out of the adsorbent bed is typically countercurrent to the $C_8$ aromatic flow, and low pressure pX, EB is collected at the outlet of the adsorption bed for further purification. At the end of this stage the non-selective void volume and molecular sieve pores are filled with a residual amount of pX/EB and the system is ready for repressurization. Prior to repressurization, a low pressure countercurrent flow of mX/oX may be used to displace the remaining pX/EB out of the adsorption vessel.

Stage 4: Repressurization of the Adsorption Vessel

The final step in the cycle is repressurization. Typically, a high pressure stream of mX/oX flowing countercurrent to the $C_8$ aromatic flow during the feed step is used to repressurize the adsorption vessel. Following repressurization, the non-selective void space contains mX/oX and the molecular sieve pores have a residual amount of pX/EB. The system is now ready to admit feed again (Stage 1).

Figure 5:
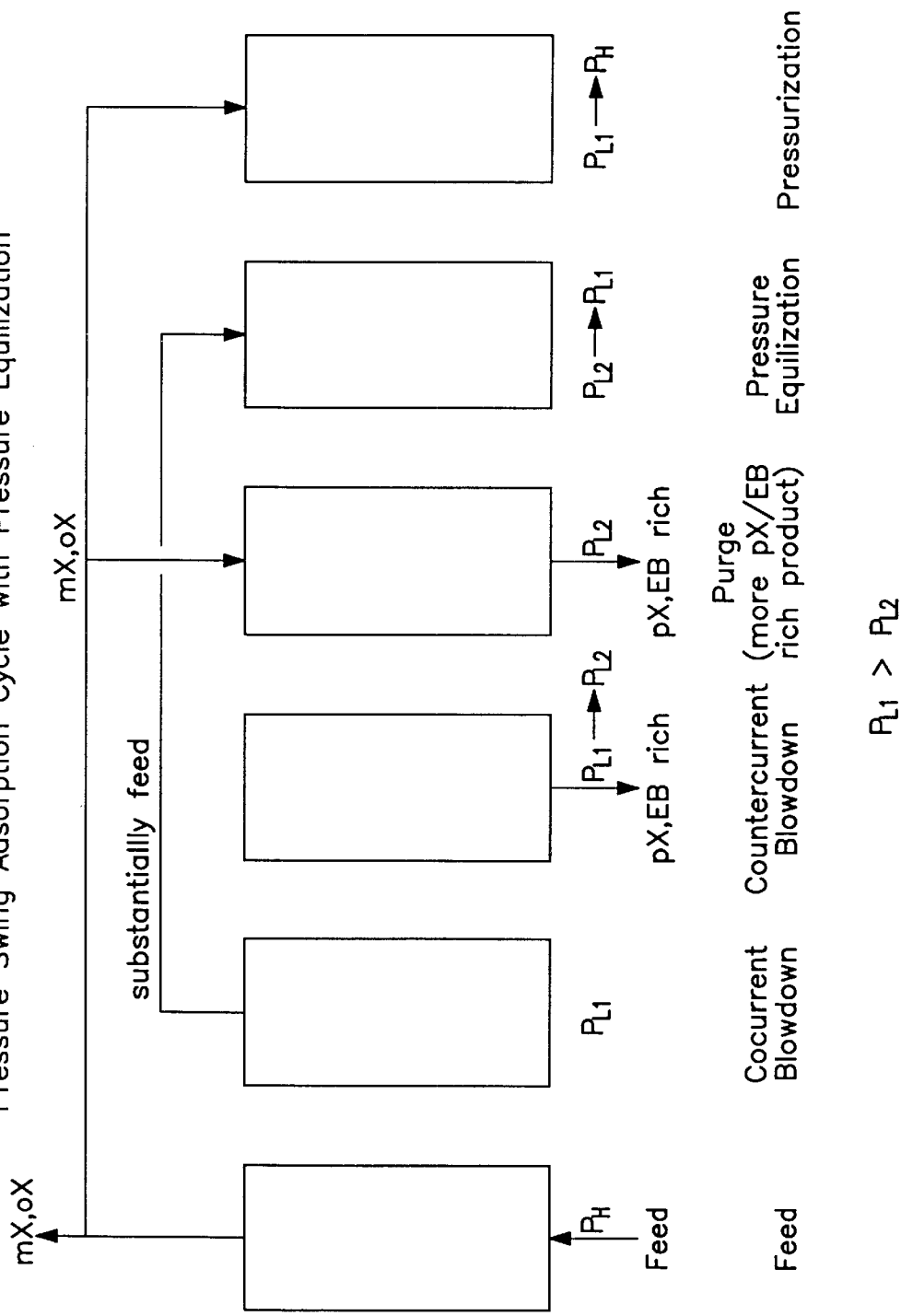
FIG. 5 illustrates a pressure swing adsorption cycle for pX/EB separation similar to that described by FIG. 2, with the exception that depressurization occurs in two steps, such that the gas from the first depressurization is used to pressurize a regenerated bed (i.e., pressure equalization).

PSA Embodiment 3: Pressure Equalization Prior to pX/EB Product Collection (FIG. 5)

This embodiment of the invention comprises a five-stage PSA cycle in which pX/EB is desorbed by lowering the absolute pressure of the adsorbent vessel in at least two steps, and then subsequently displaced from the non-selective void volume by a purge stream of substantially mX/oX.

Stage 1: Adsorption of PX and EB

In the first stage, the molecular sieve pore volume is essentially free of pX/EB and the non-selective voids (i.e., large meso-pores in the adsorbent, interstitial space between adsorbent particles, and void space in the adsorbent vessel) are filled with substantially mX/oX. A feed containing substantially $C_8$ aromatics (mX, oX, pX, EB, which may also contain some paraffins and naphthenes, $C_9+$ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This displaced mX/oX effluent stream which is substantially free of pX and EB is collected as one of the product streams for further purification of mX and oX or may be sent to a catalyst reactor for isomerization to an equilibrium xylene mixture. Introduction of feed is stopped just prior to breakthrough, and this completes Stage 1.

Stage 2: Pressure Equalization

In order to increase the purity of the pX/EB product stream collected in the subsequent stage and to conserve mechanical energy, an initial pressure reduction in the vessel takes place. The vessel is depressurized to a lower pressure ($P_{L1}$) by cocurrent blowdown and equalizing of pressure with another adsorbent bed at a lower pressure ($P_{L2}$). During this step, the feed in the non-selective void volume degasses first, resulting in a higher concentration of pX/EB in the adsorbent vessel. The second absorbent vessel is pressurized with the degassing material such that its pressure increases (from $P_{L2}$ to $P_{L1}$), such that at the end of this stage the pressure in the two vessels is equalized at $P_{L1}$).

Stage 3: Recovery of the pX/EB Stream

Following pressure equalization, the adsorbent vessel is further depressurized (e.g., via countercurrent blowdown). The purity of the exiting stream increases in px/EB during the blowdown process, such that a stream containing substantially pX/EB (based on total $C_8$ aromatics) can be obtained. At the end of Stage 3, the non-selective void volume contains substantially pX/EB and the pressure in the vessel is $P_{L2}$.

Stage 4: Removal of pX/EB in the Non-Selective Void Space

Additional pX/EB can be collected from the adsorbent vessel by displacing the pX/EB in the non-selective void space. This is typically done using a stream of substantially mX/oX, although feed can also be used. At the end of Stage 4, most of the pX/EB has been removed from the non-selective void volume and replaced with mX/oX. The pressure remains at $P_{L2}$. An adsorbent vessel in this state is used for the second adsorbent vessel in the pressure equalization step (Stage 2), such that the pressure increases from $P_{L2}$ to $P_{L1}$.

Stage 5: Repressurization to $P_H$

The final step in the cycle is to repressure the vessel from $P_{L1}$ to $P_H$ using a stream of substantially mX/oX typically flowing countercurrently to the flow during the feed stage.

Thus, at the end of the cycle, the molecular sieve pore volume is essentially free of pX/EB and the non-selective void volume contains mX/oX. The vessel is now ready to begin the cycle again (i.e., Stage 1: adsorption of pX/EB from the feed.)

Figure 2:
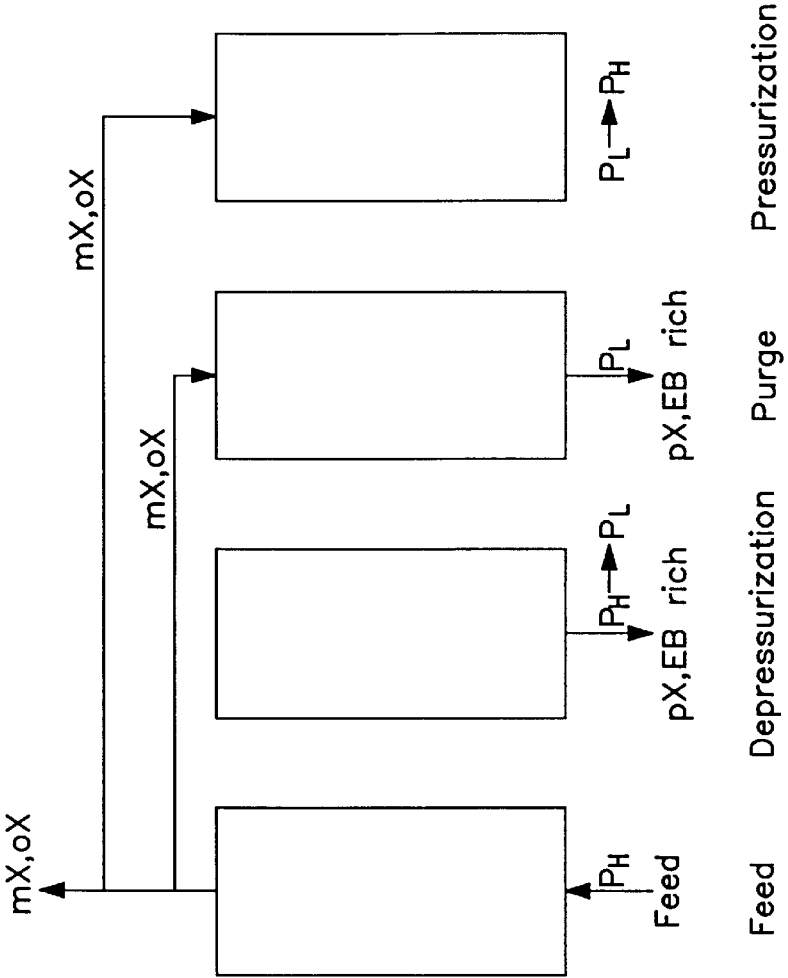
FIG. 2 is a schematic representing a four-stage pressure swing adsorption cycle for pX/EB separation in which pX/EB is desorbed by lowering the absolute pressure, and then subsequently displaced by a purge stream of substantially mX/oX.

PSA Embodiment 4: Simple 4-Stage Cycle with Purge (FIG. 2)

This cycle (shown in FIG. 2) is basically the same as Embodiment 3, except depressurization occurs in one step with no pressure equalization.

PSA Embodiment 5: Pressure Equalization Prior to Rinse

This PSA cycle is basically the same as Embodiment 3 except prior to the countercurrent blowdown step, a pX/EB rinse is used to displace the mX/oX-rich material in the void space.

The para-xylene/ethylbenzene stream produced in the PSA component of the present invention can be subjected to simulated moving bed adsorption to produce higher yields of para-xylene product at lower capital and energy cost.

Integration of PSA With Simulated Moving Bed Adsorption

Figure 7:
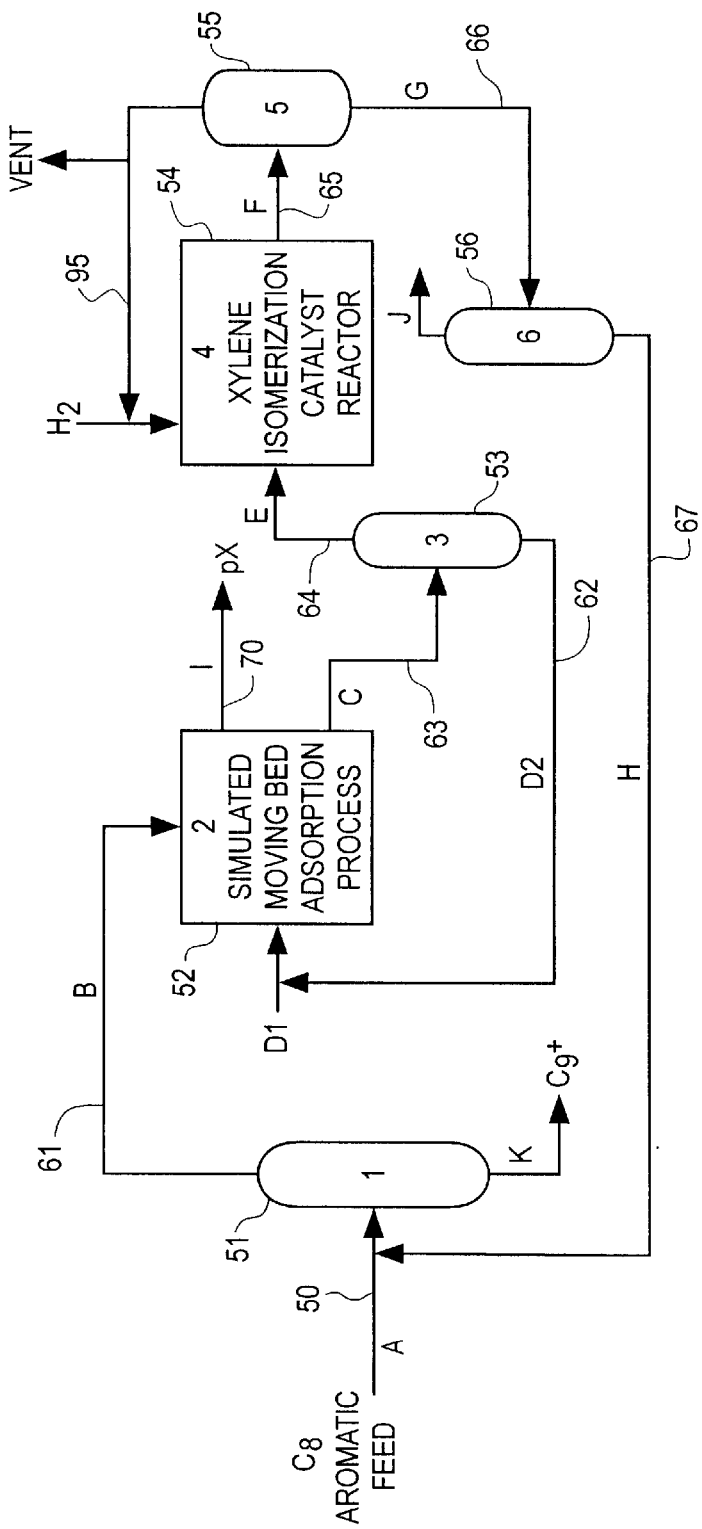
FIG. 7 shows the general flow diagram of a para-xylene production process using a current liquid chromatographic, simulated moving bed adsorbent purification process.

FIG. 7 shows the general flow diagram of a state of the art para-xylene production process using the current liquid chromatographic, simulated moving bed adsorbent (SiMBAC) process. While many sources of $C_8$ aromatics may be fed to the process, most often the $C_8$ fraction from a naphtha reformer and aromatics recovery unit containing approximately 15% ethyl benzene (EB), 22% para-xylene (pX), 50% meta-xylene (mX) and 22% ortho-xylene and varying amounts of unsaturated, linear and cyclic hydrocarbons. The feed (stream A) in line 50 is mixed with a recycle stream from the catalyst section and the combined stream (B) is sent via line 61 to the distillation section (1) 51 to remove compounds boiling at higher temperature than $C_8$ aromatics. Stream B contains predominantly $C_8$ aromatics with the pX in equilibrium with the other xylene isomers. The simulated moving bed adsorption process unit (2) 52 is generally operated to give about 95% recovery of pX (I) at a purity of greater than about 99.5%. Within the simulated moving bed section are a series of distillation towers (3) 53, which affect separation of the liquid desorbent (stream D2), which is recycled via line 62 to the process, from the unseparated $C_8$ aromatics products (C) in line 63. Fresh desorbent (stream D1) is added to the recycle desorbent (stream D2) as needed. The composition of stream E in line 64 comprises the remaining $C_8$ aromatics and contains little pX. Stream E is a para-xylene-lean stream. Stream E is sent via line 64 to the catalyst section (4) 54 where it is mixed with recycle hydrogen to establish equilibrium of the xylene isomers and to affect some EB conversion. The effluent from the reactor (stream F) in line 65 is cooled in a knockout drum (5) 55 to separate hydrogen and other light gases from the liquid (stream G) which is sent via line 65 to distillation unit (6) 56. By-products from the catalytic reactions contain compounds, which boil at lower temperature (stream J), for example, toluene, benzene and light paraffins, and are separated by distillation (6) 56. The equilibrium xylenes and heavy by-products (stream H) in line 67 are mixed with fresh feed and recycled through the process.

Figure 8:
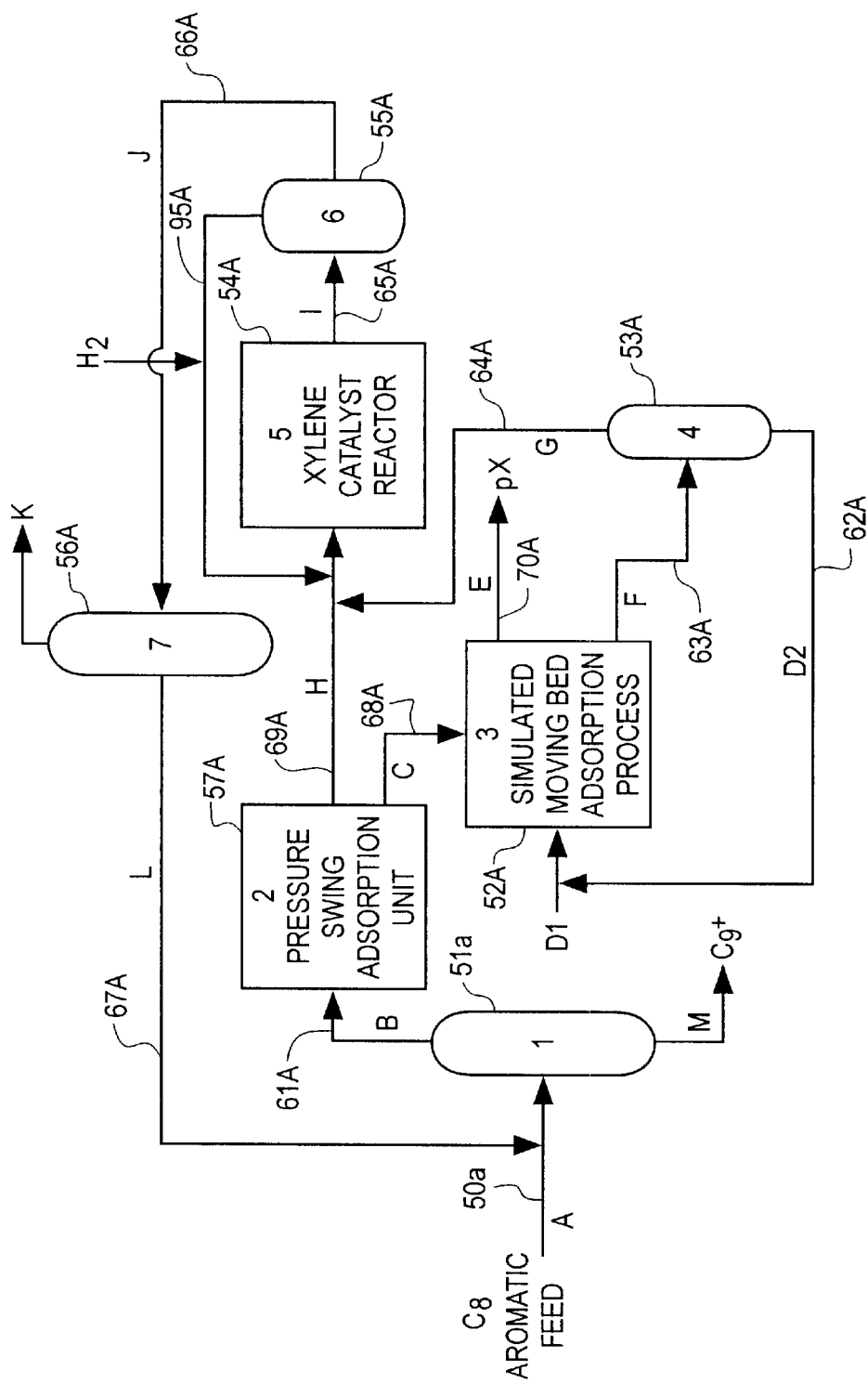
FIG. 8 shows an embodiment of the present invention which incorporates a pressure swing adsorption (PSA) unit for separating para-xylene to give a para-xylene-rich stream prior to the simulated moving bed unit.

Embodiment 1—PSA Prior to the Simulated Moving Bed Purification and a Single Catalytic Reactor FIG. 8 shows one embodiment of the current invention. The design is similar to the process described in FIG. 1 above, but incorporates a xylene pressure swing adsorption (PSA) unit prior to the simulated moving bed unit in order to provide a para-xylene-rich stream with reduced meta-xylene and ortho-xylene content to the simulated moving bed unit. The distillation towers (1) 51a and (6) 55a can be prior to the PSA unit 57a as shown in FIG. 8, or after the PSA unit 57a and immediately prior to the simulated moving bed purification unit 52a. The configuration shown in FIG. 8 is preferred since fractionation prior to adsorption in the PSA unit (2) 57a separates compounds like benzene and toluene, which will adsorb reducing the xylene capacity.

In FIG. 8, mixed xylene feed (stream A) which comprises para-xylene, meta-xylene, ortho-xylene, and, optionally, ethylbenzene is mixed with the outlet from the catalyst reactor (stream L). Heavy aromatics (stream M) are fractionated from the $C_8$ aromatics in a distillation tower (1) 51a. The xylenes isomers composition (stream B) in line 61a is in equilibrium; ca. 24 wt % (based on xylenes) and the amount of EB (typically from about 2–15%) is determined by the EB conversion in the catalyst reactor (5) 54a. In the PSA unit (2) 57a, pX and EB are concentrated relative to mX and oX. The pX concentration of the pX/EB effluent stream from the PSA unit 57a (stream C) in line 68a can be from about 30 wt % to about 85 wt % depending on the PSA cycle and operating conditions. The second steam leaving the PSA unit (stream H) in line 69a is enriched in mX and oX. Stream C can contain about 25 to about 100% of the mX and oX present in stream B and contains from 10–80% of the pX and EB present in stream B. The separation of stream B into two streams (stream C enriched in pX/EB and Stream H enriched in mX/oX) using pressure swing adsorption leads to less xylene entering into the simulated moving bed purification unit (3) 52a, thus reducing its equipment size, solvent inventory and energy requirements for recovery of purified para-xylene product (stream E) via line 70a. Stream F in line 63a is high in EB with low amounts of mX and oX and very small amounts of pX. Solvent is removed from the EB-rich stream F in distillation tower (4) 53a to give a $C_8$ aromatic stream with high EB, low mX and oX and very low pX (stream G) in line 64a. The desorbent is recycled (stream D2) in line 62a to the moving bed adsorption unit (3) 52a and mixed with fresh desorbent (stream D1). Stream G is mixed with stream H and hydrogen and sent to the catalytic reactor (5) 54a for conversion of a portion of the EB and isomerization of the xylenes.

In accordance with the process of the invention, the isomerization catalyst reactor, where the xylenes are isomerized to equilibrium and where at least a portion of the ethylbenzene may be converted to products which can be separated by fractional distillation from the $C_8$ aromatics, contains at least one catalyst that is capable of isomerizing xylenes in a mixed $C_8$ aromatic feed to produce an equilibrium mixture of xylenes and which may also possess the capability of converting at least a portion of any EB in such feed. The catalyst or combination of catalysts in the reactor can be any as are suitable for xylene isomerization and ethylbenzene conversion, as known to those skilled in the art. Examples of such catalysts are described by EP 138,617, U.S. Pat. Nos. 5,001,296, Re. 31,782, 4,098,836 and 4,899, 011 all of which are incorporated herein by reference in their entireties). Suitable isomerization conditions include a temperature of about 250° C. to about 500° C., preferably about 340° C. to about 430° C., a pressure of about atmospheric to about 400 psig, preferably in the range of about 100 psig to about 300 psig, a hydrogen to hydrocarbon mole ratio of about 0.5:1 to about 10:1, and a liquid weight hourly space velocity of about 0.5 to about 100 hr-1.

The hydrogen in the xylene catalyst reactor effluent (stream I) is separated in a knockout drum (6) 55a and recycled via line 95a to the xylene catalyst reactor (5) 54a. The liquid portion of the effluent (stream J) is separated into components lower boiling than xylenes (stream K) in fractionation tower (7) 56a. Stream L in line 67a has a portion of the EB converted and an equilibrium composition of xylenes and is mixed with fresh feed and recycled to the process.

Figure 9:
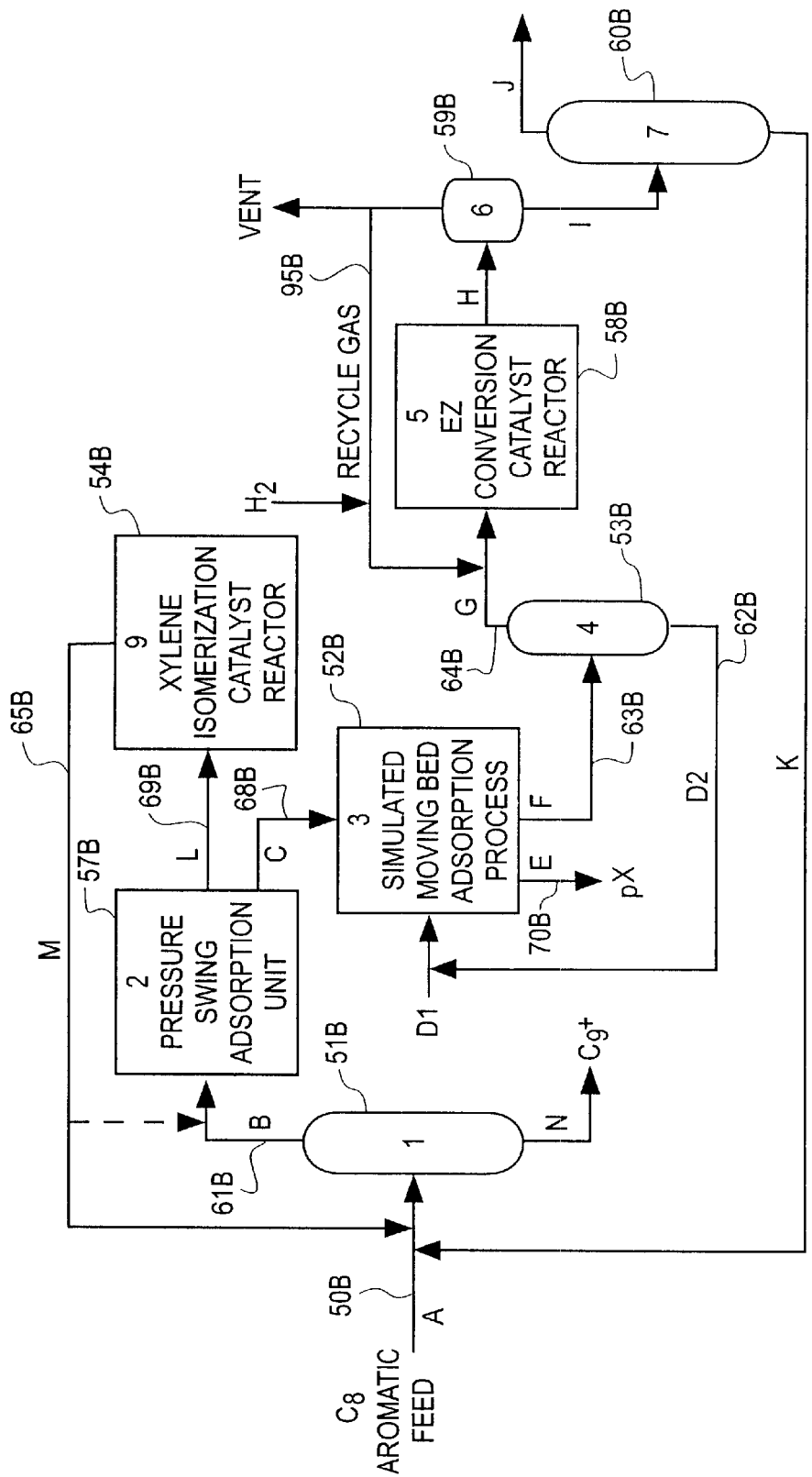
FIG. 9 shows an embodiment of the present invention wherein separate catalytic reactors are used for xylene isomerization and ethylbenzene conversion.

Embodiment 2 (EB Conversion and Xylene Isomerization in Separate Catalytic Reactors):

FIG. 9 illustrates a process where separate catalytic reactors, and possibly separate catalysts are used for isomerization and EB conversion.

In FIG. 9, mixed xylene feed (A) in line 50b is mixed with the effluent from the EB conversion catalytic reactor (5) 58b and isomerization catalytic reactor (9) 54b, stream K and stream M, respectively. Heavy aromatics (stream N) are fractionated from the $C_8$ aromatics in a distillation tower (1) 51b. The xylenes isomers composition (stream B) is in equilibrium, and the amount of EB is determined by the EB conversion in the catalyst reactor (5) 58b. In the PSA unit (2) 57b, pX and EB are concentrated relative to mX and oX. The effluent having increased pX concentration (stream C in line 68b) can be from 30–85% depending on the PSA cycle and operating conditions. The second steam leaving the PSA unit (stream L in line 69b) is enriched in mX and oX. Stream C can contain 25–100% of the mX and oX present in stream B and contains from 10–80% of the pX and EB present in stream B. The separation of B into two streams leads to less xylene entering into the simulated moving bed purification unit (3) 52b, thus reducing its equipment size, solvent inventory and energy requirements for recovery of pX (stream E in line 70b). Stream F in line 63b is high in EB with low amounts of mX and oX and very small amounts of pX. Solvent is removed from the EB rich stream in distillation tower (4) 53b to give a $C_8$ aromatic stream with high EB, low mX and oX and very low pX (stream G). The desorbent (stream D2 in line 62b) is recycled via line 62b to the moving bed adsorption unit (3) 52b and mixed with fresh desorbent (D1). Stream G is mixed with hydrogen and sent in line 64b to the EB conversion reactor (5) 58b. Effective catalysts for reactor (5) 58b include large crystal ZSM-5 and Si-selectivated catalysts. The hydrogen in the reactor effluent (H) is separated in a knockout drum (6) 59b and recycled to the EB reactor (5) 58b. The liquid portion of the effluent (stream I) is separated into components lower boiling than xylenes (stream J) in fractionation tower (7) 60b. Stream K has a portion of the EB converted with limited amounts of xylenes, and, thus is a relatively small recycle stream. Stream K is mixed with fresh feed and recycled to the process. Stream L (the mX/oX stream from the PSA unit 57b) has low pX concentration with little EB. The xylene isomerization reactor 54b is operated at low temperature and high space velocity to minimize EB conversion while establishing the xylene equilibrium. Due to the mild reaction conditions and limited by-products of these reactions the yields are higher and may be conducted in the absence of hydrogen. Stream M may be mixed with the fresh feed (A) or mixed with stream B to be recycled to the process.

The xylene isomerization catalyst in reactor (9) 54b is a catalyst that will catalyze the conversion of one xylene, such as meta-xylene or ortho-xylene, to another xylene, such as para-xylene. In particular, effective xylene isomerization catalysts will isomerize a mixture of xylenes where the xylenes are present in non-equilibrium amounts to a mixture containing, or very nearly containing, the xylenes in equilibrium amounts at the temperature used for the isomerization reaction. For example, a mixture of xylenes containing ortho-xylene, meta-xylene and para-xylene, where the para-xylene is present in less than the equilibrium amount, can be converted by an effective xylene isomerization catalyst to a mixture of xylenes where the ortho-, meta- and para-xylenes are present at or very near their equilibrium amounts.

The isomerization catalyst having activity for the isomerization of xylene in reactor (9) 54b is preferably, an acidic molecular sieve which is characterized by a constraint index in the approximate range of about 1 to about 12. Preferred molecular sieves are borosilicate molecular sieves or ZSM-type zeolite molecular sieves. The molecular sieve used is preferably dispersed on alumina, silica or another suitable matrix. The xylene isomerization catalyst may contain a hydrogenation metal selected from metals of groups VI and VIII of the Periodic Table of Elements.

The catalyst having activity for the conversion of ethylbenzene in reactor (5) 58b is preferably an acidic molecular sieve which is characterized by a constraint index in the approximate range of about 1 to about 12, more preferably it is a zeolite, preferably a crystalline aluminosilicate zeolite having a particle size of at least about 1 micron. The EB conversion catalyst may contain a hydrogenation metal selected from metals of groups VI and VIII of the Periodic Table of Elements.

The ethylbenzene conversion catalyst in reactor (5) 58b is a catalyst that selectively catalyzes the conversion of ethylbenzene in the feed mixture to another compound or compounds that can easily be removed from the product mixture. For example, within the scope of the invention, ethylbenzene conversion can occur by, but is not limited to, a transalkylation or disproportionation reaction whereby the ethylbenzene is catalytically converted to benzene and diethylbenzene, or an ethyl group from ethylbenzene is transferred to a xylene molecule thereby forming conversion products that are easily removed from the product mixture. Ethylbenzene conversion can also occur by a deethylation reaction, whereby the ethylbenzene is catalytically converted to benzene and a mixture of ethylene and ethane.

Ethylbenzene conversion catalysts suitable for use in the present invention include but are not limited to Al-MFI molecular sieve dispersed on silica and large particle size molecular sieves, particularly a ZSM-5-type of molecular sieve having a particle size of at least about 1 micron dispersed on silica, alumina, silica/alumina or other suitable support. The support material is preferably silica. Suitable catalysts based on a ZSM-type molecular sieve, for example, ZSM-5 molecular sieves, are described in U. S. Pat. No. Re. 31,782, which is incorporated herein by reference in its entirety. Other methods known to those skilled in the art, for example reaction of or coating with silicones, resulting in an XIA_parameter to EBA_parameter ratio of no more than 10, are also within the scope of the invention.

The isomerization catalyst and EB conversion catalysts used in the above embodiments of the present invention preferably contain a hydrogenation metal, such as molybdenum, platinum, palladium, rhodium, ruthenium, nickel, iron, osmium, iridium, tungsten, rhenium, and the like, dispersed on a suitable matrix. Suitable matrix materials include, but are not limited to, alumina and silica.

Embodiment 3 (No EB Conversion)

Figure 10:
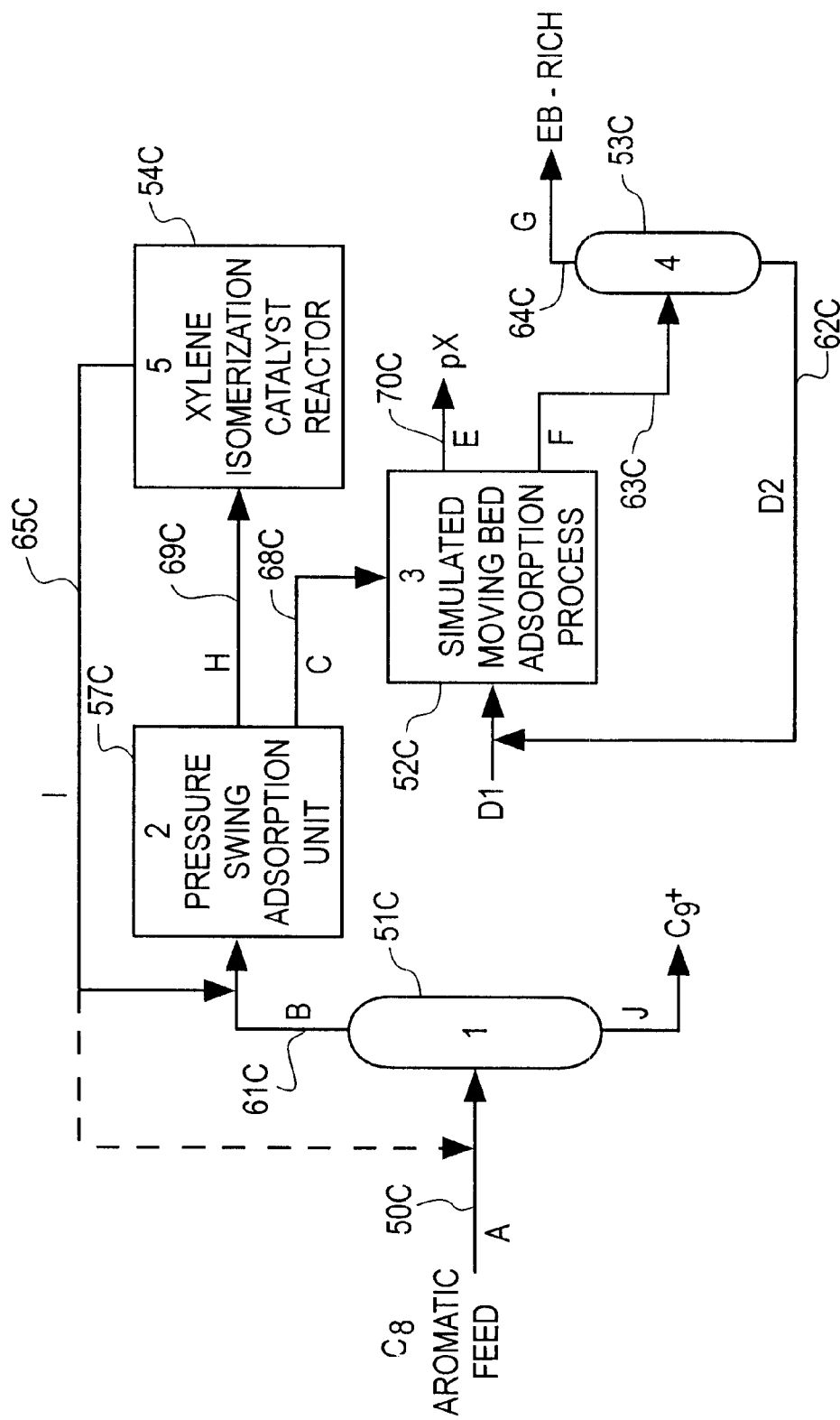
FIG. 10 shows an embodiment of the present invention wherein EB is not converted.

If the concentration of stream G in line 64b in FIG. 9 and line 64c in FIG. 10 is sufficiently low in all xylenes, then the EB can be sold as a feedstock for other processes or gasoline blending, etc. In this case no EB conversion is effected, increasing xylene yields and minimizing capital and energy costs.

In FIG. 10, mixed xylene feed (A) in line 50c is mixed with the outlet from the xylene isomerization reactor (5) 54c (stream I in line 65c). Heavy aromatics (stream J) are fractionated from the $C_8$ aromatics in a distillation tower (1)

51c. The xylenes isomers composition (stream B) is in equilibrium; and the amount of EB is determined by the amount added in the feed. In the PSA unit (2) 57c, pX and EB are concentrated relative to mX and oX. In order to minimize xylene loss to the process, the PSA is operated such that the effluent having increased pX/EB concentration (stream C in line 68c) contains small amounts of mX and oX. The separation of B into two streams (pX/EB stream C in line 68c and mX/oX stream H in line 69c) leads to less xylene entering into the simulated moving bed purification unit (3) 52c, thus reducing its equipment size, solvent inventory and energy requirements for recovery of pX (stream E in line 70c). Stream F in line 63c is high in EB with low amounts of mX and oX and very small amounts of pX. Optionally, additional product streams from the simulated moving bed effluent containing EB with mX and oX can be recycled to this section for increased recovery of xylenes. In that embodiment, solvent is removed from the EB rich stream in distillation tower (4) 53c to give a $C_8$ aromatic stream (stream G in line 64c) of high purity EB, i.e., low mX and oX and very low pX. The desorbent (D2 in line 62c) is recycled to the moving bed adsorption unit (3) 52c and mixed with fresh desorbent (stream D1). Stream H in line 69c, which is concentrated mX and oX, is sent to the catalyst reactor (5) 54c for isomerization of the xylenes. The xylene isomerization reactor is operated at low temperature and high space velocity to minimize reactions leading to loss of xylene, e.g., methyl-transfer. Due to the mild reaction conditions and limited by-products of these reactions the yields are higher and may be conducted in the absence of hydrogen. Alternatively, hydrogen can be used in the catalytic reactor if desired. Stream I in line 65c is an equilibrium mixture of xylenes or the concentration of pX may be lower than the equilibrium composition if desired. Stream I may be recycled to the PSA unit if the amount of heavy aromatic by-products is low, or may be mixed with fresh feed to remove the heavy aromatics by-products from the catalytic reactor in distillation tower (1) 51c.

In the above embodiments suitable temperature and pressure operating ranges for the simulated moving bed adsorption are those that favor liquid phase. The adsorbents are generally Y zeolite ion exchanged with K or Ba ions. The operating conditions are generally atmospheric pressure and below about 30 psi. The temperature is below the boiling point, i.e., liquid phase, typically around 150° C. or less for xylenes; however, for some compositions the temperature might be up to about 200 C.

The above embodiments demonstrate the advantages of combining pressure-swing adsorption with simulated moving bed adsorption for production of para-xylene. The advantages of this new process include lower capitol and energy costs, and higher yields of xylene. Additionally, it may be possible to conduct the isomerization reactions without costly hydrogen and eliminate the need for conversion of ethyl benzene.

The following examples will serve to illustrate certain embodiments of the invention disclosed herein. These examples should not, however, be construed as limiting the scope of the novel invention as there are many variations which may be made thereon without departing from the spirit of the disclosed invention, as those of skill in the art will recognize.

Experimental Equipment

A mass flow controller determines the Helium flow rate. A saturated flow of He, which contains EB and xylenes, is passed over the bed of adsorbent heated to the adsorption temperature. At the outlet of the bed, the gas stream is analyzed by gas chromatography to determine the composition. Any compounds not adsorbed are collected in a trap filled with silica gel with pores large enough to adsorb all compounds. After the adsorbent bed is saturated, the saturator is by-passed delivering only He to the adsorbent bed. The sample receiver is switched to a second silica gel adsorbent bed and the temperature is increased to 250° C. to affect desorption. After desorption, the receivers are removed and weighed. The receivers are then heated to desorb the adsorbed hydrocarbons, which are collected in a cold trap and subsequently analyzed by gas chromatography.

Adsorbents (1) HZSM-5

Figure 12:
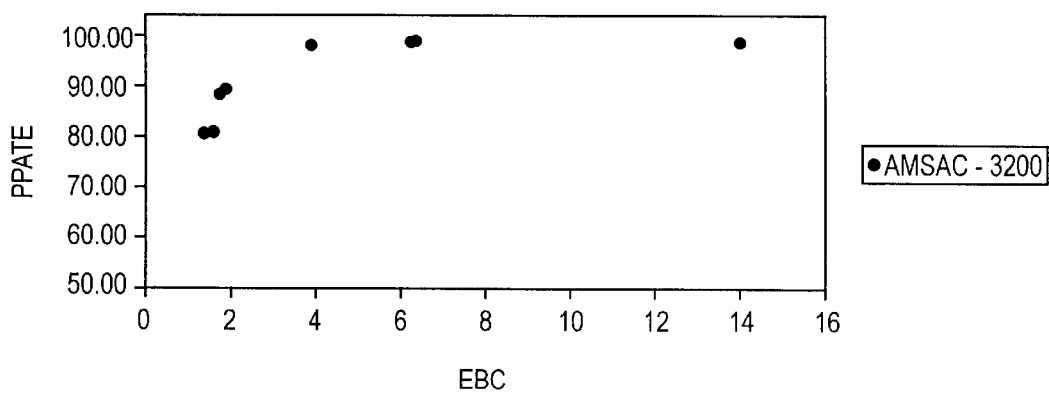
FIG. 12 shows the percent p-xylene approach to equilibrium (PPATE) under the same conditions. At low EB conversions, pX has not obtained equilibrium, while at conversions greater than about 5% EB conversion, the xylene compositions has reached equilibrium.

H-ZSM-5 containing 2% Al was a commercial sample (CBV-3020) obtained from PQ Corporation (Valley Forge Executive Mall, PO Box 840, Valley Forge, Pa. 19482).). An SEM micrograph of the sieve powder is shown in FIG. 12.

(2) HZSM-5

A second sample of HZSM-5 was prepared according to the following procedure: 20.66 g of NaOH was dissolved in 560.3 g distilled water, followed by 10.6 g of sodium aluminate ($Na_2O.Al_2O_3.3H_2O$) and 98.13 g tetrapropylammonium bromide (TPABr). The mixture was stirred until a clear solution formed. 485.9 g Nalco 2327 silica sol (40 wt % $SiO_2$) was then added and the mixture stirred for two hours. The pH of the resulting mixture was 12.5. The mixture was transferred to a Teflon-lined Parr reactor and heated at 300° F. (150° C.) for seven days with stirring (275 rpm). The reaction mixture was cooled and filtered, and the solid product washed with 10 L of distilled water. The zeolite powder was calcined to remove the template using the following program: Dry at 329° F. (165° C.) for 4 hr.; ramp to 950° F. (510° C.) over 4 hr.; hold at 950° F. (510° C.) for 12 hr.; ramp back to ambient temperature over 4 hr. An SEM micrograph of the sieve powder is shown in FIG. 7.

(3) Na-ZSM-5

Sample (2) was $Na^+$ exchanged by heating 50 g of the sieve in a solution of $NaNO_3$ (50 g in 500 ml distilled water) at 175° F. (80° C.) with stirring. The sieve was filtered and the exchange repeated with the addition of adjusting the pH to 9.5 with 50% NaOH solution. Again, the sieve was filtered and then washed by stirring for one hour in distilled water (500 ml) heated at 175° F. (80° C.). The sample was calcined using the same temperature program described above, except holding at 950° F. (510° C.) for four hours. Elemental analysis of this sample gave 1.84 wt % Na and 1.3 wt % Al. The washing step was repeated three more times to remove the excess $Na^+$. The final sample was dried for 5 hours at 220° F. (105° C.). Elemental analysis by ICP showed the washed zeolite to have 1.3 wt % Al and 1.2 wt % Na, which is a 5% molar excess of Na.

(4) Silicalite

Silicalite was prepared by adding 18.4 g NaOH to 227.6 g $H_2O$. After dissolution, 12.8 g tetrapropylammonium bromide was dissolved and 122.6 g Nalco 2327 silica sol was added and stirred for 2 hours. Concentrated $H_2SO_4$ was slowly added to achieve a pH of 13. The resulting solution was heated under autogenous pressure in a Teflon-lined autoclave for 1–7 days at 300° F.(150° C.). The crystals were filtered and washed to a neutral pH filtrate. An SEM micrograph of the sieve powder is shown in FIG. 8.

(5) Silicalite

A second sample of silicalite comprising crystals ~0.1 micron in size was prepared according to the following procedure: 1.72 g of NaOH was dissolved in 120 ml of a 1.0

M solution of tetrapropylammonium hydroxide (TPAOH). 30.0 g Cab-o-Sil M-5 silica was then added to the solution, forming a slurry. The slurry was stirred at 175° F. (80° C.) until a clear solution formed. Additional distilled water was added to make up any losses due to evaporation. The solution was transferred to a Teflon-lined Parr reactor and heated at 300° F. (150° C.) for 24 hours. The resulting mixture was centrifuged and the solids layer redispersed in distilled water. This process was repeated until the pH of the silicalite sol was <9. A portion of the silicalite sol was dried and calcined using the procedure described for sample (2), in order to obtain a solid sample for the adsorption experiments. A TEM micrograph of the sieve crystals dispersed in water is shown in FIG. 9.

(6) Ti-MFI (TS-1)

182.4 g of tetraethylorthosilicate and 2.53 g of tetraethylorthotitanate were mixed with 400.23 g of tetrapropylammonium hydroxide (20% in water). In order to remove the ethanol, the mixture was heated at 175–195° F. (80–90° C.) for 5 hours with stirring. After cooling the mixture to ambient temperature, the volume of the mixture was diluted to 600 ml with distilled water. The mixture (pH=12) was heated at 350° F. (175° C.) for 14 days with stirring (270 rpm). The white powder was washed with distilled water and calcined using the procedure described for sample (2). An SEM micrograph of the sieve powder is shown in FIG. 10.

(7) ZSM-22

Figure 11:
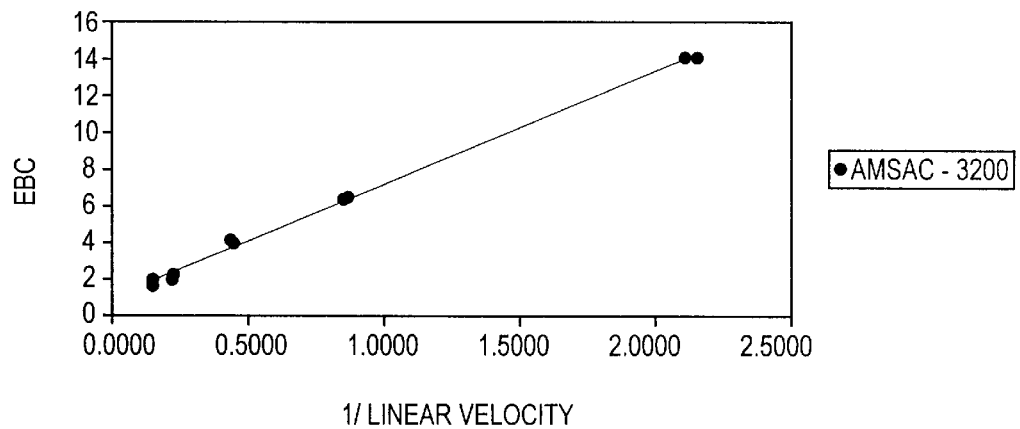
FIG. 11 shows that at the low reaction temperature of 600° F., the EB conversion (EBC) is less than about 15% and increases linearly with the inverse of the space velocity.

4.7 g of NaOH was dissolved in 119 g of distilled water. 640 g of MeOH and 220 g of Nalco 2327 silica sol (nominally 40 wt % $SiO_2$) were then added. The mixture was transferred to a 2 L autoclave and heated at 320° F. (160° C.) for 28 hours with stirring (~150 rpm). The product was collected by filtration and washed with 16 L of distilled water and calcined using the procedure described for sample (2). An SEM micrograph of the sieve powder is shown in FIG. 11.

EXAMPLE 1

Determination of $C_8$ Aromatic Adsorption Capacity of Silicalite

Figure 6:
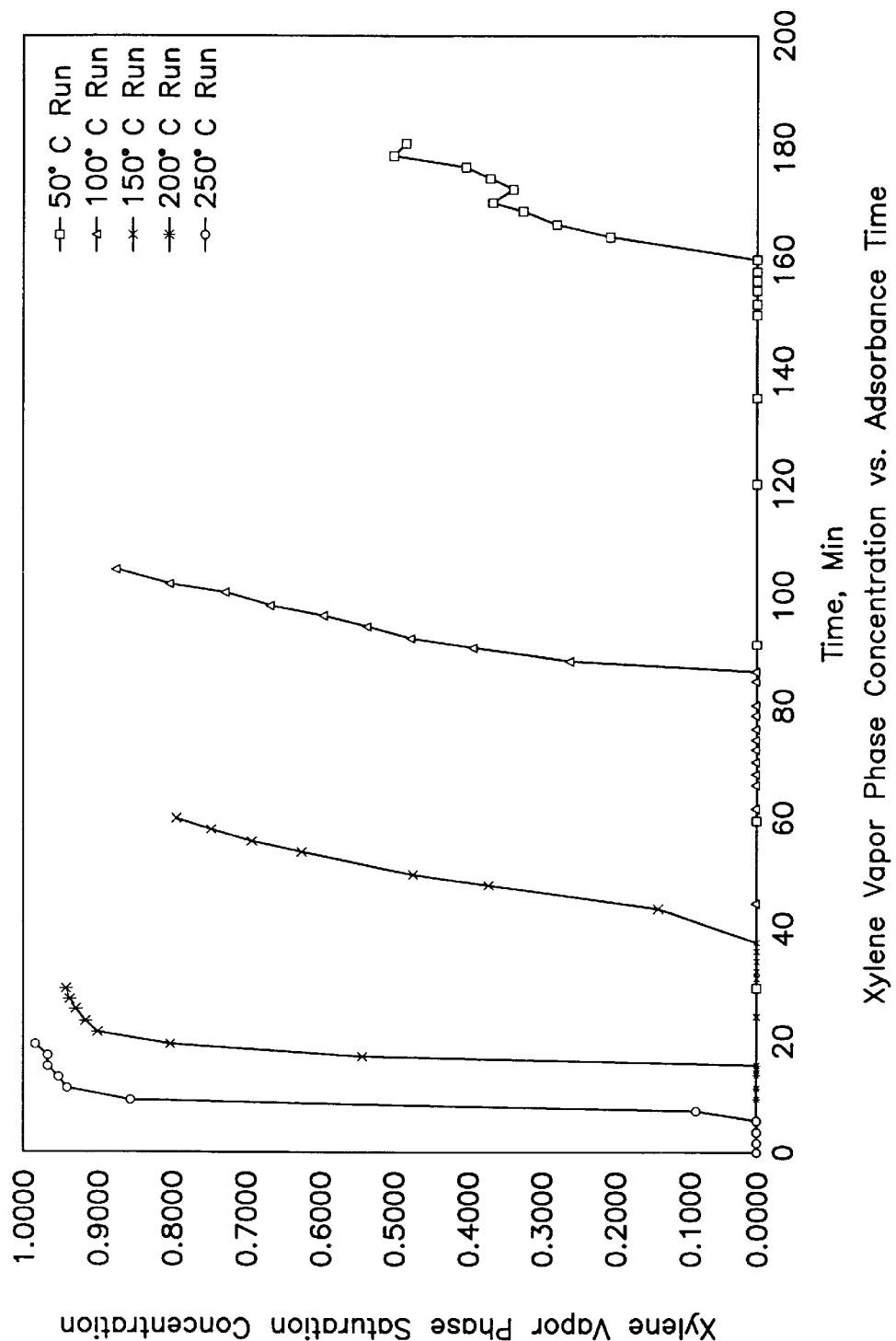
FIG. 6 shows a graph of Xylene Vapor Phase Concentrations vs. Adsorbance Time.

When a saturated stream of pX (or EB) is passed over H-ZSM-5 or silicalite at low temperature there is nearly complete adsorption. At the inlet to the reactor the concentration is equivalent to the vapor pressure, while at the outlet of the bed little pX can be detected. At saturation, the bed can no longer adsorb pX, and the concentration at the bed outlet quickly increases to the inlet concentration, as shown in FIG. 6. The amount adsorbed is proportional to the product of the flow rate, concentration and time, equation 1.

$$g\ adsorbed=[He\ flow\ (cc/min)\times Conc\ (torr/760\ torr/atm)\times 1\ atm\times t(min)\times 106\ g/mol]/22400\ cc/mol \quad (1)$$

With increasing temperature the amount of pX adsorbed on silicalite decreases as shown in Table 1. At 50° C. and a pX partial pressure of 6 torr (0.8 kPa), the saturation adsorption capacity was measured to be 9.2 wt % (92 mg/g) pX on silicalite (Adsorbent 4), while at 250° C. the adsorption capacity decreases to 0.3 wt % (3 mg/g).

TABLE 1

Adsorption of para-Xylene by Silicalite at Atmospheric Pressure (6 torr pX; 0.8 pKa)

| Adsorption Temperature, ° C. | Adsorption Capacity (mg pX/g silicalite) |
| --- | --- |
| 50 | 92 |
| 100 | 49 |
| 150 | 24 |
| 200 | 10 |
| 250 | 3 |

Single component adsorption capacities were also measured for mX, oX and EB. A comparison of the single component saturation adsorption capacity of pX, EB, mX and oX measured at 50° C. is shown in Table 2. The data demonstrates that silicalite (Adsorbent 4) has a much higher adsorption capacity for pX and EB than it does for mX and oX.

TABLE 2

Adsorption Capacity at 50° C. and atmospheric pressure (6 torr; 0.8 pKa)

| $C_8$ Aromatic Isomer | Adsorption Capacity (mg/g silicalite) |
| --- | --- |
| pX | 92 |
| EB | 63 |
| oX | <2 |
| mX | <2 |

EXAMPLE 2

Separation of Para-Xylene From Ortho-Xylene With Silicalite (Adsorbent 4)

A 1:1 mixture (3 torr:3 torr) of para-xylene and ortho-xylene was passed over the silicalite (4) adsorbent at 50° C. Monitoring the outlet stream by gas chromatography (GC) indicated that pX was adsorbed by the silicalite. Essentially ortho-xylene was not adsorbed by the silicalite, but rather passed through and was collected in a downstream trap containing amorphous silica adsorbent. Before the silicalite bed was completely saturated with para-xylene (i.e., pX breakthrough was not yet observed), the flow of xylenes was discontinued and He purged through the bed. The effluent stream was then directed to a second amorphous silica-containing trap, and the temperature of the silicalite bed was increased to 300° C. to desorb the xylenes. The adsorbed materials were recovered from the two amorphous silica traps and analyzed for xylenes by GC. The analyses are given in Table 3. The results show that para-xylene is selectively adsorbed on silicalite while ortho-xylene is essentially not adsorbed. The amount of para-xylene adsorbed was 89 mg/g which is slightly below the adsorption capacity.

TABLE 3

Silicalite: Separation of pX/oX (3 torr/3 torr) at 50° C. and Atmospheric Pressure

| Not Adsorbed | Adsorbed | Adsorbed, mg/g |
| --- | --- | --- |
| 99% oX (0.3% pX) | 97.6% pX (2.1% oX) | 89.0* (8.9 wt %) |

*Adsorption not run to saturation.

EXAMPLE 3

Separation of $C_8$ Aromatic Mixtures with Silicalite (Adsorbent 4)

A 1:1:1:1 mixture of pX:EB:mX:oX (8 torr total $C_8$) produced by bubbling He through an equimolar mixture of pX, EB, mX, and oX at atmospheric pressure) was passed over the silicalite (4) adsorbent at 50° C. Essentially mX and oX were not adsorbed on the silicalite, but passed through and were collected into the first silica trap. When the silicalite bed became saturated with pX and EB, the flow of xylenes was discontinued and He purged through the bed. The effluent was then switched to the second silica trap and the temperature of the silicalite bed increased to 300° C. to desorb the adsorbed hydrocarbons. The adsorbed materials were recovered from the two silica beds and analyzed for $C_8$ aromatics. The analysis is given in Table 4. The results show that in a mixture of EB and xylenes, pX and EB are selectively adsorbed on silicalite, while mX and oX are essentially not adsorbed.

TABLE 4

Silicalite: Separation of $C_8$ Aromatics at 50° C. and atmospheric pressure (8 torr)

| Not Adsorbed Composition | Adsorbed Composition | Wt % Adsorbed |
|---|---|---|
| 2.6% pX | 45.7% pX | 6.5% (pX and EB) |
| 5.5% EB | 51.4% EB | |
| 52.4% mX | 1.4% mX | |
| 39.2% oX | 1.1% oX | |

EXAMPLE 4

Comparison With HZSM-5: Adsorption of EB and Xylenes on H-ZSM-5 (Adsorbent 1) (CBV-3020)

Following the procedure described in Example 1, the saturation adsorption capacity of H-ZSM-5 (Adsorbent 1) was determined. Table 5 compares the saturation adsorption capacity of pX, EB, mX and oX at 50° C. The table demonstrates that for H-ZSM-5, pX and EB have a much higher adsorption capacity than mX and oX, although there is significant adsorption of the latter two.

TABLE 5

H-ZSM-5 (1): Adsorption Capacity at 50° C. and atmospheric pressure (8 torr)

| | Adsorption Capacity | |
|---|---|---|
| $C_8$ Aromatic Isomer | (Wt %) | (mg/g) |
| pX | 9.0 | 90 |
| EB | 7.5 | 75 |
| oX | 4.0 | 40 |
| mX | 4.0 | 40 |

EXAMPLE 5

Separation of Mixtures With H-ZSM-5 (Adsorbent 1), Prior Art

A 1:1:1:1 mixture (8 torr total) of pX:EB:mX:oX was passed over the H-ZSM-5 (Adsorbent 1) adsorbent at 50° C. After saturation, the flow of xylenes was discontinued and He purged through the bed. The effluent was switched to the second bed of silica and the temperature in the H-ZSM-5 bed was increased to 300° C. to desorb the xylenes adsorbed. The products were recovered and analyzed for xylenes. The analysis of the $C_8$ aromatics adsorbed on H-ZSM-5 are given in Table 6 along with results for silicalite (Adsorbent 4) under the same conditions. The results show that for the material desorbed from H-ZSM-5, the pX and EB concentrations are much lower, mX and oX are higher, and small amounts of benzene (Bz), toluene (Tol) and $C_9$ aromatics are present, indicating that some adsorbed xylenes reacted on the acid sites during high temperature desorption.

TABLE 6

Separation of $C_8$ Aromatics at 50° C. and atmospheric pressure (6 torr)

| Composition of Material Desorbed from Silicalite (4) Example 3 | Composition of Material Desorbed from H-ZSM-5 (1) Example 5 |
|---|---|
| — | 5.5% Bz |
| — | 5.9% Tol |
| 45.7% pX | 20.1% pX |
| 51.4% EB | 33.6% EB |
| 1.4% mX | 22.9% mX |
| 1.1% oX | 10.7% oX |
| — | 0.9% $C_9$ |

EXAMPLE 6

Comparison: Reaction of Adsorbed $C_8$ Aromatics on H-ZSM-5 (Adsorbent 1),

Desorption products from H-ZSM-5 (Example 5) suggest that aromatics react with acid sites in H-ZSM-5 at high desorption temperatures. To confirm, para-xylene was adsorbed at 50° C., atmospheric pressure and 6 torr partial pressure on silicalite (Adsorbent 4), and H-ZSM-5 (Adsorbent 1). The adsorbed pX was recovered by heating to 300° C. Analysis of the reaction products is given in Table 7 and indicates that there is substantial isomerization (pX to mX and oX) and transmethylation [pX to toluene and $C_9$ such as trimethylbenzene (TMB)] over H-ZSM-5, whereas, no reaction occurred over silicalite.

TABLE 7

Reactivity of Adsorbed pX

| Composition of Material Desorbed from Silicalite (4) | Composition of Material Desorbed from H-ZSM-5 (1) |
|---|---|
| pX 100% | Bz 0.1% |
| | Tol 2.1% |
| | pX 78.1% |
| | mX 14.3% |
| | oX 4.0% |
| | TMB 1.2% |

EXAMPLE 7

Adsorption/Desorption of Olefins on Silicalite and H-ZSM-5

The effect of trace olefins, which are always present in the reactants in commercial feedstreams, on the adsorption capacity was evaluated by saturation of H-ZSM-5 (Adsorbent 1), and silicalite (Adsorbent 4), at room temperature with propylene, Table 8. The quantity of adsorbed hydrocarbon was determined at temperatures up to 200° C. H-ZSM-5 readily adsorbs about 7 wt % propylene at room temperature. As the temperature increases, some propylene desorbs. Even at 200° C., however, 10% of the initial amount adsorbed remains. In order to keep olefins from lowering the adsorption capacity of H-ZSM-5 it will be necessary to operate at temperatures of above about 450° F. (about 230° C.). At these temperatures, however, significant reactions occur leading to poor selectivity. At lower temperature, desorption times are very long and olefins will reduce the adsorption capacity. In contrast silicalite does not adsorb olefins even at room temperature, thus the adsorption capacity will be unchanged with repeated adsorption/desorption cycles. The adsorption capacity of silicalite is unchanged after more than 25 adsorption/desorption cycles.

TABLE 8

Adsorption of Propylene

| Temp. | H-ZSM-5 (1) | Silicalite (4) |
|---|---|---|
| 20° C. | 6.9 wt % | 0 wt % |
| 100° C. | 5.2 wt % | — |
| 150° C. | 2.7 wt % | — |
| 200° C. | 0.6 wt % | — |

EXAMPLE 8

Effect of Xylene Partial Pressure on Adsorption Capacity at Elevated Pressure

In order to rapidly desorb para-xylene and ethylbenzene, the desorption temperature should be above about 450° F. (about 230° C.). At low partial pressure, however, the adsorption capacity is low, as seen in Table 1. The adsorption capacity at elevated temperature can be increased by increasing the adsorbate (pX and EB) partial pressure. In order to increase the pX partial pressure, the xylene saturator was replaced by an ISCO syringe pump. Additionally, a 6-way valve, heat tracing and other minor modifications were required to give instant vaporization of the xylene.

Table 9 gives the adsorption capacity of pX on silicalite (Adsorbent 4) at different temperatures and partial pressures. The data show that at constant partial pressure, the amount of pX adsorbed decreases with increasing temperature. Whereas, at high temperature, the amount of pX adsorbed can be increased by increasing the partial pressure of pX.

TABLE 9

Adsorption of pX by Silicalite at Various Temperatures and Pressures

| Ppx, torr | Temperature, ° C. | mg pX adsorbed per gram silicalite |
|---|---|---|
| 6 | 50 | 92 |
| 6 | 100 | 49 |
| 6 | 150 | 24 |
| 6 | 200 | 10 |
| 6 | 250 | 4 |
| 500 | 250 | 20 |
| 888 | 250 | 29 |
| 1996 | 250 | 60 |

EXAMPLE 9

Separation of $C_8$ Aromatic Mixtures With Silicalite at Elevated Pressure

A 1:1:1:1 mixture of pX:EB:mX:oX at a total pressure of 89 psig and 38.6 psi 250° C. The effluent composition was monitored by gas chromatography (GC). As in Example 1, when the silicalite adsorbent bed is saturated with a given isomer, the concentration of that isomer in the vapor phase at the bed outlet quickly increased to the inlet vapor phase concentration. The time required to detect that isomer at the bed outlet is proportional to the amount adsorbed on the bed.

The amount of mX and oX adsorbed was relatively small, while significantly larger amounts of pX and EB were adsorbed, Table 10. The results show that pX and EB can be selectively adsorbed at elevated temperatures and pressures in an amount comparable to pX alone (Example 8) at the same partial pressure.

TABLE 10

Adsorption Capacity of $C_8$ Aromatics at 250° C. and 1996 torr Partial Pressure (pX partial pressure about 500 torr)

| mX | 3 mg/g |
|---|---|
| oX | 3 mg/g |
| pX | 21 mg/g |
| EB | 22 mg/g |

EXAMPLE 10

Comparison of Silicalite and NaZSM-5

Non-Acidic NaZSM-5—Since HZSM-5 isomerizes and transmethylates the adsorbed xylenes, a non-acidic, sodium exchanged sample was prepared and tested. It was found that CBV-3020 could not be completely exchanged; therefore, another sample of HZSM-5 (Adsorbent 2), was prepared containing 1.3 wt % Al. This material was completely exchanged with Na, such that no acid sites remained to give Na-ZSM-5 (Adsorbent 3). The adsorption capacity for pX was 115 mg/g at 50° C. and atmospheric pressure. Increasing the temperature to 250° C. decreased the adsorption capacity to 26.3 mg/g. Furthermore, at 250° C., only pX was observed in the effluent, confirming complete exchange of the acid sites with $Na^+$.

This sample was also tested with a saturated gas mixture (1 atm) of $C_8$ aromatics in He at 50° C., as was done with silicalite and HZSM-5. The adsorbate was desorbed and analyzed by GC. A comparison of these results with those obtained for silicalite (Adsorbent 4) is given in Table 11. The mX and oX present in the desorbate for NaZSM-5 is not due to isomerization (as verified with the feed containing only pX). Thus, the NaZSM-5 sample has a lower pX adsorption selectivity than the silicalite sample tested, but a greater total capacity at these conditions.

To determine whether the decrease in pX selectivity is due to decreasing crystal size, a silicalite sample (Adsorbent 5), having a crystal size of approximately 0.1 μm was also prepared and tested. The composition of the adsorbate is compared with that of the adsorbates obtained for large crystal silicalite (Adsorbent 4), small crystal HZSM-5 (Adsorbent 1), and small crystal NaZSM-5 (Adsorbent 3) in Table 12. The size of the small crystal silicalite sample was determined by Transmission Electron Microscopy (TEM) to be approximately 0.1 μm. The crystal size of the two ZSM-5 samples was determined by Scanning Electron Microscopy (SEM) to be approximately 0.1–0.4 μm. The size of the large crystal silicalite sample was also determined by SEM to have an average minimum dimension of greater than 0.5 μm.

TABLE 11

Comparison of Silicalite and NaZSM-5
(Feed is a He stream saturated with $C_8$ aromatics (oX, mX, pX, and EB); adsorbed at 50° C. and 1 atm)

| Silicalite (4) | NaZSM-5 (3) |
|---|---|
| 65 mg adsorbate/g Silicalite | 88 mg adsorbate/g NaZSM-5 |

| Adsorbate Compositions | |
|---|---|
| 1.4% mX | 9.5% mX |
| 1.1% oX | 7.7% oX |
| 45.7% pX | 45.0% pX |
| 51.4% EB | 37.8% EB |

TABLE 12

Comparison of Adsorbates for Large Crystal Silicalite with Small Crystal Silicalite, HZSM-5, and NaZSM-5 at 50° C. and 1 atm. (Feed is a He stream saturated with $C_8$ aromatics (oX, mX, pX, and EB);

| Silicalite (4) (>0.5 µm average minimum dimension) 65 mg adsorbate/g Silicalite | Silicalite (5) (about 0.1 µm) 83 mg adsorbate/g Silicalite | HZSM-5 (1) (about 0.1–0.4 µm) 85 mg adsorbate/g HZSM-5 | NaZSM-5 (3) (about 0.1–0.4 µm) 88 mg adsorbate/g NaZSM-5 |
|---|---|---|---|
| Adsorbate Compositions | | | |
| 1.4% mX | 14.8% mX | 17.0% mX | 9.5% mX |
| 1.1% oX | 13.7% oX | 14.3% oX | 7.7% oX |
| 45.7% pX | 33.3% pX | 31.4% pX | 45.0% pX |
| 51.4% EB | 38.2% EB | 37.3% EB | 37.8% EB |

The selectivities for the small silicalite, HZSM-5 and NaZSM-5 are very similar, with the selectivity of the NaZSM-5 sample for pX being somewhat better. All of these selectivities are significantly lower than that obtained for the large crystal silicalite. These results are consistent with a crystal size effect on selectivity.

EXAMPLE 11

Selective Adsorption With TS-1 (Ti-MFI) and ZSM-22

Using the same method as given in Example 3, the adsorption capacity at 50° C. and 8 torr total $C_8$ aromatics was measured for TS-1 (Adsorbent 6) and ZSM-22 (Adsorbent 7). Both samples showed selective adsorption of pX and EB over mX and oX. Results are given in Table 13.

TABLE 13

Adsorption on TS-1 and ZSM-22
Feed is a He stream saturated with $C_8$ aromatics (oX, mX, pX, and EB); adsorbed at 50° C. and 8 torr $C_8$ aromatics

| TS-1 (6) 58 mg adsorbate/g sieve | ZSM-22 (7) 46 mg adsorbate/g sieve |
|---|---|
| Adsorbate Compositions | |
| 3.1% mX | 4.8% mX |
| 3.3% oX | 5.4% oX |
| 42.8% pX | 39.9% pX |
| 50.8% EB | 50.0% EB |

EXAMPLE 12

This example illustrates that the pX-depleted stream gives lower xylene loss in the isomerization reactor, which increases the overall yield of pX for the unit."

A comparison was done for a xylene isomerization catalyst run with a mixed xylene feed containing 10 wt % pX and a mixed xylene feed containing 1 wt % pX. The catalyst was an aluminosilicate/borosilicate catalyst system with a molybdenum hydrogenation metal. Such catalysts are described in EP 0 923 512 incorporated herein by reference in its entirety. Results in Table 14 below show that xylene loss decrease when the amount of pX in the feed is reduced.

TABLE 14

| | Feed A | Feed B |
|---|---|---|
| wt % pX in feed | 1% | 10% |
| % Xylene Loss at 50% EB conversion | 0.7 | 1.1 |
| % Xylene Loss at 80% EB conversion | 1.8 | 2.3 |

EXAMPLE 13

Catalyst Tests

A commercial xylene isomerization catalyst, 20% borosilicate molecular sieve with 80% γ-alumina binder (AMSAC 3200), was loaded into a small, continuous-flow, fixed-bed catalyst testing unit. The operating pressure was 150 psig at a hydrogen-to-hydrocarbon ratio of 4 and at a reaction temperature of 600° F. The feed was a plant mixed xylene feed with a composition: 5.2% lights (benzene, toluene, paraffin and naphthenes), 12.9% EB, 8.5% pX, 49.1% mX, 21.3% oX and 3.0% heavy aromatics. The feed rate was adjusted to give a WHSV from 2–30 $hr^{-1}$. The results of the tests are given in FIGS. 11–14. FIG. 11, shows that at the low reaction temperature of 600° F., the EB conversion (EBC) is less than about 15% and increases linearly with the inverse of the space velocity.

FIG. 12 shows the percent p-xylene approach to equilibrium (PPATE) under the same conditions. At low EB conversions, pX has not obtained equilibrium, while at conversions greater than about 5% EB conversion, the xylene compositions has reached equilibrium.

Figure 13:
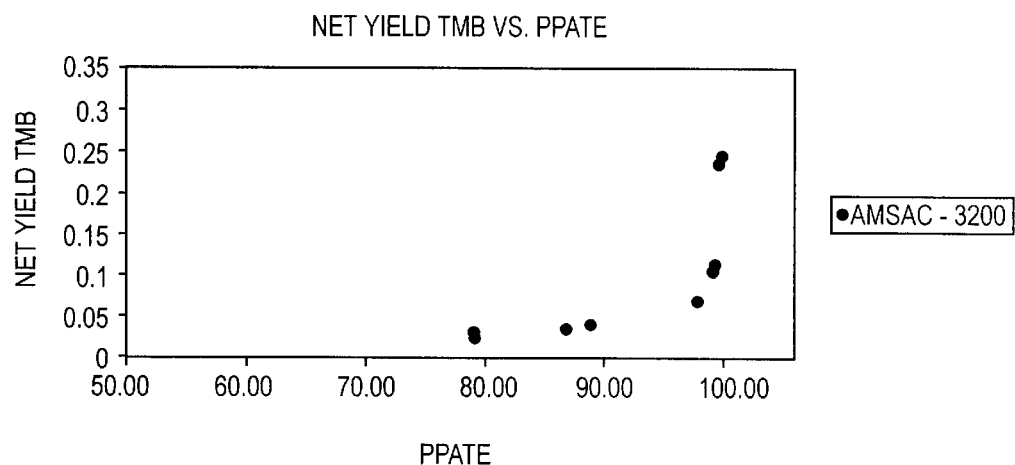
FIG. 13 shows that the yield loss from trimethylbenzenes (formed from the reaction of 2 xylenes to form toluene and trimethylbenzene) is low when the xylene composition is below the equilibrium composition but increases with increasing EB conversion.
Figure 14:
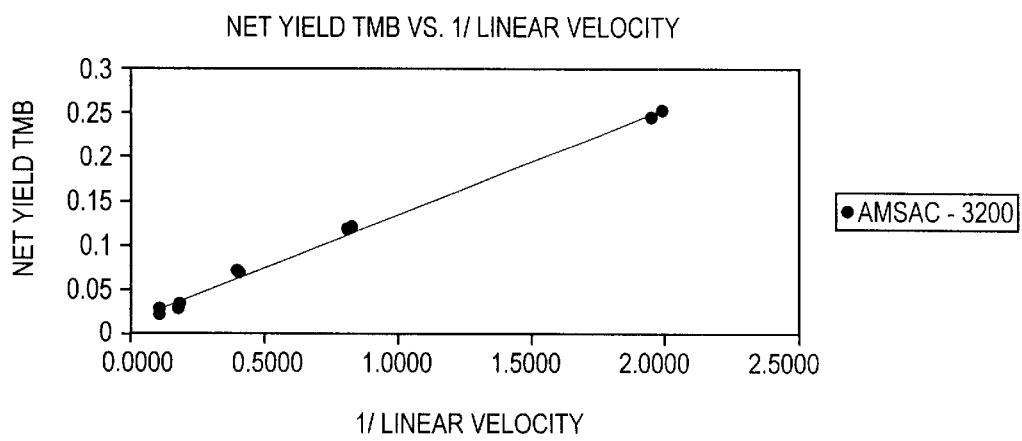
FIG. 14 also shows that the yield loss from trimethylbenzenes (formed from the reaction of 2 xylenes to form toluene and trimethylbenzene) is low when the xylene composition is below the equilibrium composition but increases with increasing EB conversion.

FIGS. 13 and 14 show that the yield loss from trimethylbenzenes (formed from the reaction of 2 xylenes to form toluene and trimethyl-benzene) is low when the xylene composition is below the equilibrium composition but increases as the xylene composition approaches equilibrium and continues to increase with an increase in the reciprocal of the space velocity.

The catalyst tests demonstrate that the yield loss to trimethyl-benzenes and toluene can be minimized if reaction conditions are mild such that the xylene compositions are at or near equilibrium. Under these conditions, however, the EB conversion is low, thus EB must be removed from the process by other than catalytic conversion. pX process designs, therefore, which eliminate EB without catalytic reaction minimize the xylene yield loss by catalytic reaction, see for example the scheme given in FIG. 4.

The catalyst test results demonstrate that the proposed process designs provide advantages over the existing pX processes, which use simulated moving bed adsorption for purification.

With the present invention, we can run at low EB conversion, low isomerization activity to minimize xylene loss, yet, nevertheless, with PSA we can still get high pX concentrations for sending to the purification section.

In a conventional process, one must react the EB from the Xylene stream. At high EB conversions, there is also xylene loss (as toluene and trimethylbenzene). The figures show that at low EB conversion there is low loss of Xylenes (as indicated by the lower trimethylbenzene formation). In current processes this would also give low xylene isomerization conversion (80–95% PPate). With less para-xylene there is less recovery of product and more recycle. All of these things are undesirable.

With PSA, it is possible to run at low isomerization activity. Since only PX (and EB) are adsorbed, the PX/EB stream sent to the Simulated Moving bed purification is still rich in PX, thus the unit is still small and process yields are high. Also, MX and OX are still not sent to the purification system, keeping the Simulated Moving Bed small relative to an existing unit. The other stream from the Simulated Moving bed unit would be high in EB with some small amounts of PX, MX and OX. The EB could be sent for sale (probably as gasoline) thus there would be no EB catalyst reactor, or it could be sent to a Catalyst reactor for conversion of EB to Benzene, or perhaps EB to xylenes (catalysts called naphthene pool catalysts). The former would give EB conversion with minimum xylene loss (since there are low concentrations of xylenes in that stream), while the latter step would give a net increase in xylene while minimizing the yield loss that normally occurs with naphthene pool catalysts when EB is converted to xylene in a mixed aromatic stream.

A primary advantage is that the isomerization catalysts can be run under different conditions (at less than isomerization equilibrium) to minimize yield losses. Also, EB can be removed from the feed by routes other than catalytic conversion. The EB can be sold for gasoline blending or, if further purified, might be sold as a chemical product. Additionally, the high EB stream would be an ideal feed for a naphthene pool catalyst to give additional xylenes. All these options are not practical or possible without using PSA to treat the feed prior to use of simulated moving bed adsorption.

That which is claimed is:

1. A process for separating and recovering para-xylene from a gaseous mixture comprising $C_8$ aromatic hydrocarbons, the process comprising:
   (a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;
   (b) sending at least a portion of the para-xylene-rich stream to a simulated moving bed adsorption unit and subjecting said para-xylene-rich stream to simulated moving bed adsorption to produce a para-xylene product stream and an ethylbenzene-rich $C_8$ aromatic stream;
   (c) sending at least a portion of the meta-xylene and ortho-xylene-rich stream to an isomerization unit and isomerizing said stream to produce an isomerizate having an increased concentration of para-xylene;
   (d) recycling at least a portion of the isomerizate from step (c) to step (a);
   (e) removing any desorbent from the ethylbenzene-rich $C_8$ aromatic stream from step (b) and then contacting at least a portion of the ethylbenzene-rich $C_8$ aromatic stream with an ethylbenzene conversion catalyst and converting said stream to produce an effluent stream comprising mixed xylenes; and
   (f) recycling at least a portion of the effluent stream comprising mixed xylenes from step (e) to step (a).

2. The process of claim 1 wherein the gaseous mixture comprising meta-xylene, ortho-xylene, para-xylene, and ethylbenzene is contacted with an ethylbenzene conversion catalyst to remove at least a portion of the ethylbenzene prior to being subjected to pressure swing adsorption in step (a).

3. The process of claim 1 wherein at least a portion of the ethylbenzene-rich $C_8$ aromatic stream from step (b) is combined with the meta-xylene and ortho-xylene-rich effluent stream from step (a) and contacted with a xylene isomerization catalyst system which is capable of isomerizing xylenes in a mixed $C_8$ aromatics feed and converting at least a portion of any ethylbenzene in such $C_8$ aromatics feed to produce an effluent stream comprising mixed xylenes which is then recycled to step (a).

4. The process of claim 1 wherein any desorbent is removed from the ethylbenzene-rich $C_8$ aromatic stream from step (b) to give an ethylbenzene-rich $C_8$ product stream.

5. The process of claim 1 wherein the adsorbent used in the pressure swing adsorption of step (a) comprises a para-selective, non-acidic molecular sieve.

6. The process of claim 1 wherein the adsorbent used in the pressure swing adsorption of step (a) comprises a para-selective, non-acidic, medium pore molecular sieve.

7. The process of claim 6 wherein the molecular sieve used in the pressure swing adsorption of step (a) comprises orthorhombic crystals of silicalite having an average minimum dimension of at least about 0.2 μm.

8. The process of claim 1 wherein the pressure swing adsorption in step (a) is operated at a temperature of at least about 350° F. and a pressure of at least about 30 psia.

9. The process of claim 1 wherein the pressure swing adsorption in step (a) is operated at a temperature of from about 350° F. to about 750° F. and a pressure of from about 30 psia to about 400 psia.

10. The process of claim 1 wherein the pressure swing adsorption in step (a) is operated at a temperature of from about 400° F. to about 650° F. and a pressure of from about 50 psia to about 300 psia.

11. The process of claim 1 wherein a Y zeolite is used as adsorbent in the simulated moving bed adsorption in step (b).

12. The process of claim 11 wherein the Y zeolite is ion-exchanged exchanged with ions selected from the group consisting of potassium ions and barium ions.

13. The process of claim 1 wherein the simulated moving bed adsorption in step (b) is conducted at a temperature of up to about 150° C.

14. The process of claim 1 wherein the simulated moving bed adsorption in step (b) is conducted at a temperature of up to about 200° C.

15. The process of claim 1 wherein the meta-xylene and ortho-xylene-rich effluent stream produced in step (a) contains no more than about 15 mole percent of para-xylene based on total $C_8$ aromatics.

16. The process of claim 1 wherein the meta-xylene and ortho-xylene-rich effluent stream produced step (a) contains no more than about 10 mole percent of para-xylene based on total $C_8$ aromatics.

17. The process of claim 1 wherein the meta-xylene and ortho-xylene-rich effluent stream produced in step (a) contains no more than about 5 mole percent of para-xylene based on total $C_8$ aromatics.

18. The process of claim 1 wherein the para-xylene-rich effluent stream collected in step (a) contains no more than a total of about 25 mole percent of meta-xylene and ortho-xylene based on total $C_8$ aromatics.

19. The process of claim 1 wherein the para-xylene-rich effluent stream collected in step (a) contains no more than a total of about 10 mole percent of meta-xylene and ortho-xylene based on total $C_8$ aromatics.

20. The process of claim 1 wherein the para-xylene-rich effluent stream collected in step (a) contains no more than a total of about 5 mole percent of meta-xylene and ortho-xylene based on total $C_8$ aromatics.

21. The process of claim 1 wherein the para-selective adsorbent defines non-selective voids and the pressure swing adsorption of step (a) further comprises a pressure swing adsorption process for separating para-xylene and ethylbenzene from the gaseous mixture comprising $C_8$ aromatics containing para-xylene, ethylbenzene, meta-xylene and ortho-xylene under substantially isothermal conditions comprising:
   (1a) adsorbing the gaseous mixture onto an adsorbent comprising a para-selective adsorbent capable of selectively adsorbing para-xylene and ethylbenzene at a temperature and pressure at which at least 0.01 grams of para-xylene and ethylbenzene may be adsorbed per gram of adsorbent;
   (1b) producing a first effluent stream comprising a mixture of ortho-xylene and meta-xylene, which contains no more than a total of about 25 mole percent para-xylene and ethylbenzene based on total $C_8$ aromatics;
   (1c) removing at least a portion of the gaseous mixture from the non-selective voids;
   (1d) selectively desorbing para-xylene and ethylbenzene from the para-selective adsorbent by decreasing partial pressure of para-xylene and ethylbenzene; and
   (1e) collecting a stream comprising para-xylene and ethylbenzene from step (1d) which contains no more than a total of about 50 mole percent of meta-xylene and ortho-xylene based on total $C_8$ aromatics.

22. The process of claim 21 wherein the adsorbent comprises a para-selective, non-acidic medium pore zeolite, the temperature is from about 350° F. to about 750° F., and the pressure is from about 30 psia to about 400 psia.

23. The process of claim 21 wherein the mixture of ortho-xylene and meta-xylene produced in step (1b) contains no more than a total of about 15 mole percent of para-xylene and ethylbenzene based on total $C_8$ aromatics, and the stream containing para-xylene and ethylbenzene collected in step (1e) contains no more than a total of about 25 mole percent of meta-xylene and ortho-xylene based on total $C_8$ aromatics.

24. The process of claim 1 wherein the pressure swing adsorption in step (a) comprises a pressure swing adsorption process for separating para-xylene and ethylbenzene from the gaseous mixture comprising $C_8$ aromatics containing para-xylene, ethylbenzene, meta-xylene and ortho-xylene under substantially isothermal conditions comprising:
   (1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the adsorbent bed to an outlet, and containing a purge gas substantially free of $C_8$ aromatic compounds;
   (1b) flowing the gaseous mixture comprising xylenes and ethylbenzene into the adsorbent bed through one or more of the vessel inlets, and collecting effluent from one or more of the outlets and segregating at least a fraction of the purge gas substantially free of $C_8$ aromatic compounds while selectively adsorbing para-xylene and ethylbenzene from the gaseous mixture under substantially isothermal conditions in the bed;
   (1c) collecting from one or more of the outlets a first effluent product comprising m-xylene and o-xylene which contains no more than a total of about 25 mole percent of para-xylene and ethylbenzene based on total $C_8$ aromatics;
   (1d) replacing the gaseous mixture flowing into the adsorbent bed through one or more inlets with the purge gas while maintaining substantially isothermal conditions in the adsorbent bed, and collecting from one or more of the outlets an effluent gaseous mixture until effluent at the outlet contains no more than a total of about 50 mole percent of m-xylene and o-xylene based on total $C_8$ aromatics;
   (1e) collecting from one or more of the outlets a second effluent product comprising ethylbenzene and para-xylene which contains no more than a total of about 50 mole percent of m-xylene and o-xylene based on total $C_8$ aromatics; and
   (1f) repeating steps (1b) through (1e) at least once wherein the second effluent product comprising ethylbenzene and para-xylene comprises at least a portion of the gaseous mixture for said repeating of step (1b).

25. The process of claim 24 wherein the adsorbent comprises a para-selective, non-acidic medium pore zeolite, the temperature is from about 350° F. to about 750° F., the pressure is from about 30 psia to about 400 psia, and the purge gas is selected from the group consisting of $C_1$–$C_4$ alkanes, He, $CO_2$, hydrogen, nitrogen, argon and mixtures thereof.

26. The process of claim 24 wherein the mixture of ortho-xylene and meta-xylene produced in step (1b) contains no more than a total of about 15 mole percent of para-xylene and ethylbenzene based on total $C_8$ aromatics, and the stream containing para-xylene and ethylbenzene collected in step (1e) contains no more than a total of about 25 mole percent of meta-xylene and ortho-xylene based on total $C_8$ aromatics.

27. The process of claim 24 wherein steps (1b) through (1e) are carried out under substantially isothermal conditions at temperatures in a range upward from about 450° F., wherein steps (1b) through (1e) are carried out under constant pressure at a pressure of at least about 80 psia, and wherein steps (1b) through (1e) are repeated with a cycle time of from about 2 minutes to about 200 minutes.

28. The process of claim 24 wherein at least a portion of the effluent gaseous mixture collected in step (1d) is admixed with the gaseous mixture in subsequent cycles.

29. The process of claim 24 wherein the purge gas comprises hydrogen, and wherein steps (1b) through (1e) are repeated with a cycle time of from about 3 minutes to about 30 minutes under substantially isothermal conditions at a temperature of about 350° F. to about 750° F. and at constant operating pressure at a pressure of at least about 30 psia.

30. The process of claim 24 wherein the flow of said purge gas is countercurrent to the flow of said gaseous mixture.

31. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(1b) flowing the gaseous mixture comprising xylene isomers and ethylbenzene into the adsorbent bed through one or more inlets, and displacing the meta-xylene and ortho-xylene in the vessel while selectively adsorbing ethylbenzene and para-xylene from the gaseous mixture under substantially isothermal conditions in the adsorbent bed;

(1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of the gaseous mixture at the pressure for adsorption;

(1d) replacing the gaseous mixture flowing into the bed through one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(1e) reducing the pressure to desorb ethylbenzene and para-xylene from the para-selective adsorbant while maintaining substantially isothermal conditions in the bed; and (1f) collecting a second effluent product comprising ethylbenzene and para-xylene which contains no more than a total of about 50 mole percent of meta-xylene and ortho-xylene based on total $C_8$ aromatics.

32. The process of claim 31 wherein the flow of said para-xylene and ethylbenzene purge gas is countercurrent to the flow of the gaseous mixture.

33. The process of claim 31 wherein the para-xylene and ethylbenzene effluent flow during depressurization is countercurrent to the flow of the gaseous mixture.

34. The process of claim 31 wherein the flow of meta-xylene and ortho-xylene to pressurize the vessel is countercurrent to the feed gas flow.

35. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing at least two adsorbent beds containing an ad or adsorbent comprising a para-selective adsorbent defining non-selective voids which exhibits capacity to selectively adsorb and desorb para-xylene and ethylbenzene under substantially isothermal conditions at operating pressure, disposed in connected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(1b) flowing the gaseous mixture comprising xylene isomers and ethylbenzene into the adsorbent bed in the first vessel through one or more inlets, and displacing the meta-xylene and ortho-xylene in the vessel while selectively adsorbing ethylbenzene and para xylene from the gaseous mixture under substantially isothermal conditions in the adsorbent bed;

(1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of the gaseous mixture at the pressure for adsorption;

(1d) stopping the flow of the gaseous mixture and reducing the pressure in the first vessel sufficiently to permit removal of at least a portion of the gaseous mixture from the non-selective voids while maintaining substantially isothermal conditions in the bed by equalizing the pressure in the first vessel with the pressure in the second vessel which is at a lower pressure;

(1e) further reducing the pressure in the first vessel to desorb ethylbenzene and para-xylene while maintaining substantially isothermal conditions in the bed; and (1f) collecting a second effluent product comprising ethylbenzene and para-xylene which contains no more than a total of about 50 mole percent of meta-xylene and ortho-xylene based on total $C_8$ aromatics.

36. The process of claim 35 wherein, following step (1f), a purge gas comprising meta-xylene and ortho-xylene is added to the first vessel to displace para-xylene and ethylbenzene in the non-selective voids, and an effluent comprising the para-xylene and ethylbenzene is collected.

37. The process of claim 35 wherein prior to step (1d) a rinse comprising para-xylene and ethylbenzene is introduced into the vessel to displace meta-xylene and ortho-xylene in non-selective voids.

38. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(1b) flowing the gaseous mixture comprising xylene isomers and ethylbenzene into the adsorbent bed through one or more inlets and displacing the meta-xylene and ortho-xylene in the vessel while selectively adsorbing ethylbenzene and para-xylene from the gaseous mixture under substantially isothermal conditions in the adsorbent bed (1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of the gaseous mixture at the pressure for adsorption;

(1d) stopping the flow of the gaseous mixture and reducing operating pressure to a pressure at which para-xylene and ethylbenzene desorb from the para-selective adsorbent while maintaining substantially isothermal conditions in the bed; and (1e) collecting a second effluent product comprising ethylbenzene and para-xylene which contains no more than a total of about 50 mole percent of meta-xylene and ortho-xylene based on total $C_8$ aromatics.

39. The process of claim 38 wherein, following step (1e), a purge gas of meta-xylene and ortho-xylene is added to the first vessel to displace para-xylene and ethylbenzene in the non-selective voids, and an effluent comprising the para-xylene and ethylbenzene is collected.

40. The process of claim 6 wherein the para-selective, non-acidic medium pore molecular sieve is selected from the group of molecular sieve structure types consisting of MFI, TON, MTT, MEL, EUO, and FER.

41. The process of claim 1 wherein the adsorbent comprises a para-selective adsorbent and a binder.

42. The process of claim 41 wherein the binder is selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

43. The process of claim 1 wherein the adsorbent contains about 5 to about 100 weight percent para-selective adsorbent.

44. A process for separating and recovering para-xylene from a gaseous mixture comprising $C_8$ aromatic hydrocarbons, the process comprising:

(a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream, and a para-xylene-rich effluent stream;

(b) sending at least a portion of the para-xylene-rich stream to a simulated moving bed adsorption unit and subjecting said para-xylene-rich stream to simulated moving bed adsorption to produce a para-xylene product stream and an ethylbenzene-rich C8 aromatic stream;

(c) sending at least a portion of the meta-xylene and ortho-xylene-rich stream to an isomerization unit and isomerizing said stream to produce an isomerizate having an increased concentration of para-xylene;

(d) recycling at least a portion of the isomerizate from step (c) to step (a);

(e) removing any desorbent from the ethylbenzene-rich $C_8$ aromatic stream from step (b) and then contacting at least a portion of the ethylbenzene-rich $C_8$ aromatic stream with an ethylbenzene conversion catalyst and converting said stream to produce an effluent stream comprising mixed xylenes; and (f) recycling at least a portion of the effluent stream comprising mixed xylenes from step (e) to step (a).

45. The process of claim 44 wherein the adsorbent used in the pressure swing adsorption in step (a) comprises a para-selective, non-acidic, medium pore molecular sieve, and wherein the pressure swing adsorption in step (a) is operated at a temperature of at least about 350° F. and a pressure of at least about 30 psia.

* * * * *